United States Patent
Konishi et al.

(10) Patent No.: US 11,525,132 B2
(45) Date of Patent: Dec. 13, 2022

(54) LIGASE MUTANT

(71) Applicant: AJINOMOTO CO., INC., Tokyo (JP)

(72) Inventors: Miwa Konishi, Kawasaki (JP); Shohei Kajimoto, Kawasaki (JP); Yusuke Hagiwara, Kawasaki (JP); Yasuhiro Mihara, Kawasaki (JP); Shogo Nakano, Shizuoka (JP); Tomoharu Motoyama, Shizuoka (JP); Sohei Ito, Shizuoka (JP)

(73) Assignee: AJINOMOTO CO., INC., Tokyo (JP)

( * ) Notice: Subject to any disclaimer, the term of this patent is extended or adjusted under 35 U.S.C. 154(b) by 12 days.

(21) Appl. No.: 17/210,094

(22) Filed: Mar. 23, 2021

(65) Prior Publication Data
US 2021/0301280 A1    Sep. 30, 2021

(30) Foreign Application Priority Data

Mar. 25, 2020  (JP) .............................. JP2020-055033
Jan. 26, 2021  (JP) .............................. JP2021-010565

(51) Int. Cl.
*C12N 9/00* (2006.01)
*C12N 15/11* (2006.01)
*C12P 19/34* (2006.01)

(52) U.S. Cl.
CPC ................ *C12N 9/93* (2013.01); *C12N 15/11* (2013.01); *C12P 19/34* (2013.01); *C12N 2310/14* (2013.01)

(58) Field of Classification Search
None
See application file for complete search history.

(56) References Cited

FOREIGN PATENT DOCUMENTS

WO     2008/094599 A2     8/2008

OTHER PUBLICATIONS

Chauleau, M., & Shuman, S. Kinetic mechanism of nick sealing by T4 RNA ligase 2 and effects of 3'-OH base mispairs and damaged base lesions. RNA, 19(12) 1840-1847.
Nandakumar, J., Shuman, S., Lima, C. D. (2006). RNA ligase structures reveal the basis for RNA specificity and conformational changes that drive ligation forward. Cell, 6;127(1)71-84.
Ho, C. K., & Shuman, S. (2002). Bacteriophage T4 RNA ligase 2 (gp24.1) exemplifies a family of RNA ligases found in all phylogenetic domains. PNAS, 1;99(20)12709-14.
Nandakumar, J., Ho, C. K., Lima, C. D., Shuman, S. (2004). RNA substrate specificity and structure-guided mutational analysis of bacteriophage T4 RNA ligase 2. J. Biol. Chem., 23;279(30)31337-47.
Nandakumar, J. & Shuman, S. (2004). How an RNA ligase discriminates RNA versus DNA damage. Mol. Cell., 22;16(2)211-21.
Nandakumar, J. & Shuman, S. (2005). Dual mechanisms whereby a broken RNA end assists the catalysis of its repair by T4 RNA ligase 2. J. Biol. Chem., 24;280(25)23484-9.
Yin, S., Ho, C. K., Shuman, S. (2003). Structure-function analysis of T4 RNA ligase 2. J. Biol. Chem., 16;278(20)17601-8.
Yin, S., Kiong Ho, C., Miller, E. S., Shuman, S. (2004). Characterization of bacteriophage KVP40 and T4 RNA ligase 2. Virology, 5;319(1)141-51.
Extended European Search Report dated Aug. 31, 2021 in European Patent Application No. 21164084.2, 7 pages.
Database EMBL [Online], "*Escherichia phage* vB_EcoM_JB75 RNA ligase 2 ID—AXC34018; SV 1; linear; genomic DNA; STD; PHG; 1005 BP." Retrieved from EBI Accession No. EMBL:AXC34018, XP002803946, Jul. 24, 2018, 1 page.
Database JPO Proteins [Online], "JP 2017046695-A/533: Antibacterial Phage, Phage Peptides and Methods of Use Thereof." Retrieved from EBI Accession No. JPOP:LX657126, Jun. 29, 2017, 1 page.
Database JPO Proteins [Online], "WO 2019156020-A/21: Method for producing nucleic acid molecule." Retrieved from EBI Accession No. JPOP:MB951381, Nov. 29, 2019, 1 page.
RNA lipase, Rn12 family (*Escherichia phage* T4( Protein Sequence, NCBI Reference Sequence: NP_049790.1, National Center for Biotechnology Information, U.S. National Library of Medicine.
Chauleau, M., & Shuman, S. Kinetic mechanism of nick seating by T4 RNA ligase 2 and effects of 3'-OH base mispairs and damaged base lesions. RNA, 19(12) 1840-1847.
Nandakomar, J., Shuman, S., Lima, C. D. (2006). RNA figwse structures reveal the basis for RNA specificity and conformational changes that drive ligation forward. Cell, 6;127(1)71-84.
Ho, C. K., & Shuman, S. (2002). Bacteriophade T4 RNA ligase 2(gp24.1) exemplifies a family of RNA ligases found in all phylogenebc domains. PNAS, 1;99(20)12709-14.
Nandakumar, J., Ho, C. K., Lima, C. D. , Shuman, S. (2004). RNA substrate specificity and structure-guided mutational analysts of bacteriophage. T4 RNA ligase 2 J. Biol. Chem, 23;279(30)31337-47.
Nandakomar, J. & Shuman, S. (2004). How an RNA ligase discriminates RNA versus DNA damage. Mol. Cell., 22;16(2)211-21.
Nandakurnar, J. & Shuman. S. (2005). Dual mechanisms whereby a broken RNA end assists the catlaysis of its repair by T4 RNA ligase 2. J. Biol. Chem., 24,280(25)23484-9.
Yin, S., Ho, C. K., Shuman, S. (2003). Structure-function analysis of T4 RNA ligase 2. J Biol. Chem., 16;278(20)17901-8.
Yin; S., Kiang Ho, C. Miller. E. S., Shuman, S. (2004). Characterization of bactertophage KVP40 and T4 RNA ligase 2. Virology, 5;319(1)141-51.

*Primary Examiner* — Kagnew H Gebreyesus
(74) *Attorney, Agent, or Firm* — Oblon, McClelland, Maier & Neustadt, L.L.P.

(57) ABSTRACT

Ligase mutants of the following (1), (2), or (3):
(1) a ligase mutant comprising an amino acid sequence showing 95% or more identity to the amino acid sequence of SEQ ID NO: 1, and having a nucleic acid-linking activity;
(2) a ligase mutant comprising an amino acid sequence showing 90% or more identity to the amino acid sequence of SEQ ID NO: 2, and having a nucleic acid-linking activity; or
(3) a ligase mutant comprising an amino acid sequence showing 97% or more identity to the amino acid sequence of SEQ ID NO: 3, and having a nucleic acid-linking activity, have excellent properties.

16 Claims, 4 Drawing Sheets

Specification includes a Sequence Listing.

FIG. 1

1) Amino acid sequence of Mut1

MFKKYSSLENHYNSKFIEKLYSLGLTGGEWVAREKIHGTNFSLIIERDKVTCAKRTGPILPAE
DFYGYEIVLKKYDDSIKAVQDIMETSAAVSYQVFGEFAGGGIQKGVDYGEKDFYVFDIIVNT
ESGDVTYVDDYMMESFCNTFGFKMAPLLGRGTFEELIKLPNDLDSVVQDYNVTVDADLVE
ANKCVFDAEAKGENTAEGYVLKPCYPKWLPNGNRVAIKCKNSKFSEKKKSDKPIKAKVELS
EADNKLVGILACYVTLNRVNNVISKIGEIGPKDFGKVMGLTVQDILEETSREGITLTQADNPS
LIKKELVKMVQDVLRPAWIELVS (SEQ ID NO: 1)

2) Amino acid sequence of Mut2

MFKKYSSLENHYNSKFIEKLYSLGLTSGEWVAREKIHGTNFSLIIERDKVTCAKRTGPILPAE
DFYGYEIIMKKYDDAIKAVQDIMETSAAVSYQVFGEFAGGGIQKGVDYGDKDFYVFDIIVTT
EDGEVSYMDDYEMESFCNTFGFKMAPLLGRGSFEDLIKLPNDLDSVVNDYNVTVDADLVE
ANKCVFDAEAKGENTAEGYVLKPCYPKWLPNGNRVAIKCKNSKFSEKKKSDKPIKAKVELS
EADNDLVGILAEYVTWNRVSNVISKIGEVGPKDFGKVMGLTVQDILEEASREGITLTQAENP
SLVKKELVKMVMDTLREAWIEL (SEQ ID NO: 2)

3) Amino acid sequence of Mut3

MFKKYSSLENHYNSKFIEKLYSLGLTGGEWVAREKIHGTNFSLIISDDKVTCAKRSGPILPAE
DFFGYEIIVKNYADAIRAVQDIMETSAVVSYQVFGEFAGPGIQKNVDYGDKDFYVFDIIVTTE
SGDVTYVDDYMMESFCNTFKFKMAPLLGRGKFEELIKLPNDLDSVVNDYNFTVDHAGLVD
ANKCVFNAEAKGEVFTAEGYVLKPCYPSWLRNGNRVAIKCKNSKFSEKKKSDKRIKAKVEL
SEADNELVGILACYVTLNRVNNVISKIGEVGPKDFGKVMGLTVQDILEEASREGITLTQADN
WSLIKKELVKMVQDVVREAWIEL (SEQ ID NO: 3)

FIG. 2

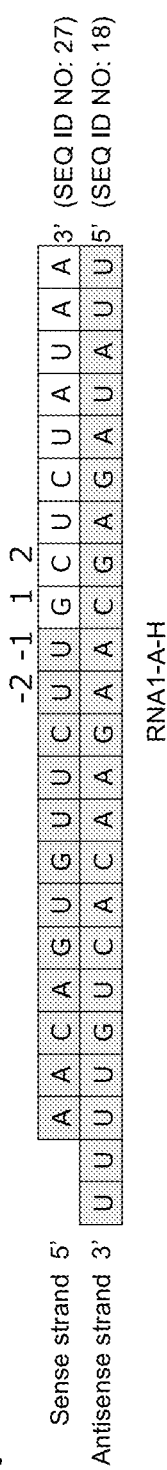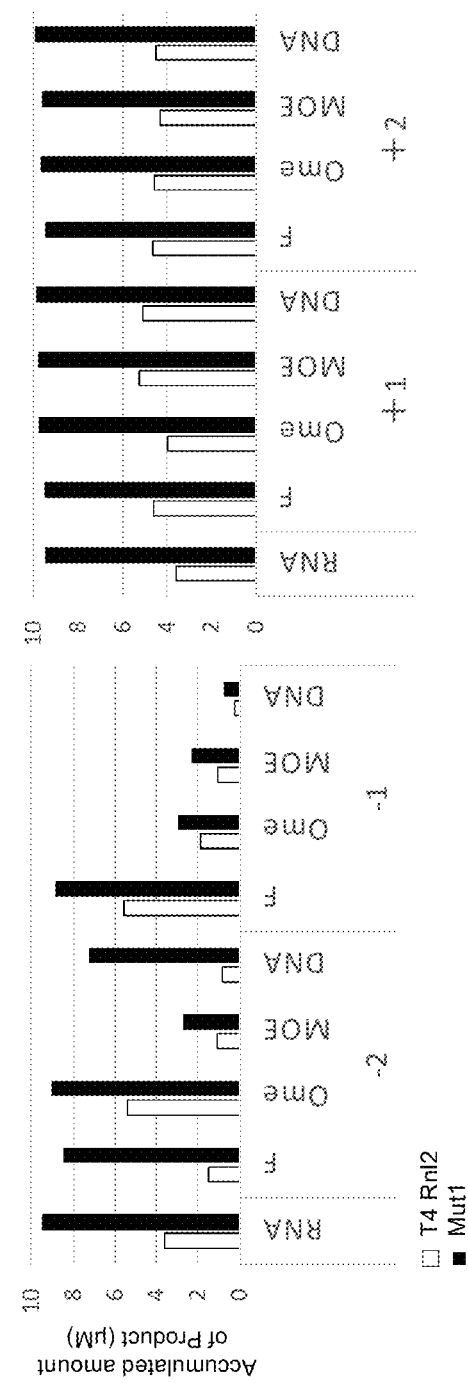
FIG.4A
FIG.4B

SEQUENCE LISTING

```
<160> NUMBER OF SEQ ID NOS: 29

<210> SEQ ID NO 1
<211> LENGTH: 332
<212> TYPE: PRT
<213> ORGANISM: Artificial Sequence
<220> FEATURE:
<223> OTHER INFORMATION: Ligase mutant

<400> SEQUENCE: 1

Met Phe Lys Lys Tyr Ser Ser Leu Glu Asn His Tyr Asn Ser Lys Phe
1               5                   10                  15

Ile Glu Lys Leu Tyr Ser Leu Gly Leu Thr Gly Gly Glu Trp Val Ala
            20                  25                  30

Arg Glu Lys Ile His Gly Thr Asn Phe Ser Leu Ile Ile Glu Arg Asp
        35                  40                  45

Lys Val Thr Cys Ala Lys Arg Thr Gly Pro Ile Leu Pro Ala Glu Asp
    50                  55                  60

Phe Tyr Gly Tyr Glu Ile Val Leu Lys Lys Tyr Asp Asp Ser Ile Lys
65                  70                  75                  80

Ala Val Gln Asp Ile Met Glu Thr Ser Ala Ala Val Ser Tyr Gln Val
                85                  90                  95

Phe Gly Glu Phe Ala Gly Gly Gly Ile Gln Lys Gly Val Asp Tyr Gly
            100                 105                 110

Glu Lys Asp Phe Tyr Val Phe Asp Ile Ile Val Asn Thr Glu Ser Gly
        115                 120                 125

Asp Val Thr Tyr Val Asp Asp Tyr Met Met Glu Ser Phe Cys Asn Thr
    130                 135                 140

Phe Gly Phe Lys Met Ala Pro Leu Leu Gly Arg Gly Thr Phe Glu Glu
145                 150                 155                 160

Leu Ile Lys Leu Pro Asn Asp Leu Asp Ser Val Val Gln Asp Tyr Asn
                165                 170                 175

Val Thr Val Asp Ala Asp Leu Val Glu Ala Asn Lys Cys Val Phe Asp
            180                 185                 190

Ala Glu Ala Lys Gly Glu Asn Thr Ala Glu Gly Tyr Val Leu Lys Pro
        195                 200                 205

Cys Tyr Pro Lys Trp Leu Pro Asn Gly Asn Arg Val Ala Ile Lys Cys
    210                 215                 220

Lys Asn Ser Lys Phe Ser Glu Lys Lys Ser Asp Lys Pro Ile Lys
225                 230                 235                 240

Ala Lys Val Glu Leu Ser Glu Ala Asp Asn Lys Leu Val Gly Ile Leu
                245                 250                 255

Ala Cys Tyr Val Thr Leu Asn Arg Val Asn Asn Val Ile Ser Lys Ile
```

```
                260                 265                 270
Gly Glu Ile Gly Pro Lys Asp Phe Gly Lys Val Met Gly Leu Thr Val
            275                 280                 285

Gln Asp Ile Leu Glu Glu Thr Ser Arg Glu Gly Ile Thr Leu Thr Gln
290                 295                 300

Ala Asp Asn Pro Ser Leu Ile Lys Lys Glu Leu Val Lys Met Val Gln
305                 310                 315                 320

Asp Val Leu Arg Pro Ala Trp Ile Glu Leu Val Ser
            325                 330

<210> SEQ ID NO 2
<211> LENGTH: 330
<212> TYPE: PRT
<213> ORGANISM: Artificial Sequence
<220> FEATURE:
<223> OTHER INFORMATION: Ligase mutant

<400> SEQUENCE: 2

Met Phe Lys Lys Tyr Ser Ser Leu Glu Asn His Tyr Asn Ser Lys Phe
1               5                   10                  15

Ile Glu Lys Leu Tyr Ser Leu Gly Leu Thr Ser Gly Glu Trp Val Ala
            20                  25                  30

Arg Glu Lys Ile His Gly Thr Asn Phe Ser Leu Ile Ile Glu Arg Asp
        35                  40                  45

Lys Val Thr Cys Ala Lys Arg Thr Gly Pro Ile Leu Pro Ala Glu Asp
    50                  55                  60

Phe Tyr Gly Tyr Glu Ile Ile Met Lys Lys Tyr Asp Asp Ala Ile Lys
65                  70                  75                  80

Ala Val Gln Asp Ile Met Glu Thr Ser Ala Ala Val Ser Tyr Gln Val
            85                  90                  95

Phe Gly Glu Phe Ala Gly Gly Ile Gln Lys Gly Val Asp Tyr Gly
            100                 105                 110

Asp Lys Asp Phe Tyr Val Phe Asp Ile Ile Val Thr Thr Glu Asp Gly
        115                 120                 125

Glu Val Ser Tyr Met Asp Asp Tyr Glu Met Glu Ser Phe Cys Asn Thr
    130                 135                 140

Phe Gly Phe Lys Met Ala Pro Leu Leu Gly Arg Gly Ser Phe Glu Asp
145                 150                 155                 160

Leu Ile Lys Leu Pro Asn Asp Leu Asp Ser Val Val Asn Asp Tyr Asn
            165                 170                 175

Val Thr Val Asp Ala Asp Leu Val Glu Ala Asn Lys Cys Val Phe Asp
        180                 185                 190

Ala Glu Ala Lys Gly Glu Asn Thr Ala Glu Gly Tyr Val Leu Lys Pro
    195                 200                 205

Cys Tyr Pro Lys Trp Leu Pro Asn Gly Asn Arg Val Ala Ile Lys Cys
210                 215                 220

Lys Asn Ser Lys Phe Ser Glu Lys Lys Ser Asp Lys Pro Ile Lys
225                 230                 235                 240

Ala Lys Val Glu Leu Ser Glu Ala Asp Asn Asp Leu Val Gly Ile Leu
            245                 250                 255

Ala Glu Tyr Val Thr Trp Asn Arg Val Ser Asn Val Ile Ser Lys Ile
        260                 265                 270

Gly Glu Val Gly Pro Lys Asp Phe Gly Lys Val Met Gly Leu Thr Val
    275                 280                 285

Gln Asp Ile Leu Glu Glu Ala Ser Arg Glu Gly Ile Thr Leu Thr Gln
```

```
            290             295             300
Ala Glu Asn Pro Ser Leu Val Lys Lys Glu Leu Val Lys Met Val Met
305                 310                 315                 320

Asp Thr Leu Arg Glu Ala Trp Ile Glu Leu
                325                 330

<210> SEQ ID NO 3
<211> LENGTH: 332
<212> TYPE: PRT
<213> ORGANISM: Artificial Sequence
<220> FEATURE:
<223> OTHER INFORMATION: Ligase mutant

<400> SEQUENCE: 3

Met Phe Lys Lys Tyr Ser Ser Leu Glu Asn His Tyr Asn Ser Lys Phe
1               5                   10                  15

Ile Glu Lys Leu Tyr Ser Leu Gly Leu Thr Gly Gly Glu Trp Val Ala
                20                  25                  30

Arg Glu Lys Ile His Gly Thr Asn Phe Ser Leu Ile Ile Ser Asp Asp
            35                  40                  45

Lys Val Thr Cys Ala Lys Arg Ser Gly Pro Ile Leu Pro Ala Glu Asp
50                  55                  60

Phe Phe Gly Tyr Glu Ile Ile Val Lys Asn Tyr Ala Asp Ala Ile Arg
65                  70                  75                  80

Ala Val Gln Asp Ile Met Glu Thr Ser Ala Val Val Ser Tyr Gln Val
                85                  90                  95

Phe Gly Glu Phe Ala Gly Pro Gly Ile Gln Lys Asn Val Asp Tyr Gly
            100                 105                 110

Asp Lys Asp Phe Tyr Val Phe Asp Ile Ile Val Thr Thr Glu Ser Gly
        115                 120                 125

Asp Val Thr Tyr Val Asp Asp Tyr Met Met Glu Ser Phe Cys Asn Thr
130                 135                 140

Phe Lys Phe Lys Met Ala Pro Leu Leu Gly Arg Gly Lys Phe Glu Glu
145                 150                 155                 160

Leu Ile Lys Leu Pro Asn Asp Leu Asp Ser Val Val Asn Asp Tyr Asn
                165                 170                 175

Phe Thr Val Asp His Ala Gly Leu Val Asp Ala Asn Lys Cys Val Phe
            180                 185                 190

Asn Ala Glu Ala Lys Gly Glu Val Phe Thr Ala Glu Gly Tyr Val Leu
        195                 200                 205

Lys Pro Cys Tyr Pro Ser Trp Leu Arg Asn Gly Asn Arg Val Ala Ile
210                 215                 220

Lys Cys Lys Asn Ser Lys Phe Ser Glu Lys Lys Ser Asp Lys Arg
225                 230                 235                 240

Ile Lys Ala Lys Val Glu Leu Ser Glu Ala Asp Asn Glu Leu Val Gly
                245                 250                 255

Ile Leu Ala Cys Tyr Val Thr Leu Asn Arg Val Asn Asn Val Ile Ser
            260                 265                 270

Lys Ile Gly Glu Val Gly Pro Lys Asp Phe Gly Lys Val Met Gly Leu
        275                 280                 285

Thr Val Gln Asp Ile Leu Glu Glu Ala Ser Arg Glu Gly Ile Thr Leu
290                 295                 300

Thr Gln Ala Asp Asn Trp Ser Leu Ile Lys Lys Glu Leu Val Lys Met
305                 310                 315                 320

Val Gln Asp Val Val Arg Glu Ala Trp Ile Glu Leu
```

<210> SEQ ID NO 4
<211> LENGTH: 996
<212> TYPE: DNA
<213> ORGANISM: Artificial Sequence
<220> FEATURE:
<223> OTHER INFORMATION: Nucleotide sequence encoding ligase mutant

<400> SEQUENCE: 4

```
atgttcaaga aatacagtag ccttgagaat cactacaaca gcaaattcat cgaaaaactc      60
tactccttag ccctcactgg tgtgaatgg gttgcgcgtg agaaaatcca tggtacgaac     120
ttctctctta tcattgaacg cgataaagtg acctgtgcga acgcacggg acctattctg     180
ccggctgaag acttttatgg gtatgagatt gtgctgaaga atacgacga ctcgataaaa     240
gccgtacagg atatcatgga aacctctgca gcagtgagct atcaggtctt ggcgaatttt     300
gcaggggggtg gtattcagaa aggcgtggat tacggagaga aagacttcta cgtgttcgat     360
attatcgtga acacagaatc aggggatgtg acctatgtcg atgactatat gatggagtcg     420
ttttgcaaca cctttggctt caaaatggct ccgctgttag gtcgtggcac gtttgaagag     480
ctgatcaaac tgccgaatga tctggactct gttgtacagg attataacgt caccgttgat     540
gcggacttgg tagaagcgaa taaatgtgtg tttgatgccg aagcgaaagg tgagaatacc     600
gctgaagggt atgttctgaa accgtgctat ccgaaatggc tgccaaatgg caatcgcgtt     660
gccatcaaat gcaagaactc caagtttagc gaaaagaaaa aatcggacaa accgattaaa     720
gcgaaagttg aactgagtga agcagacaat aaactggtag aatcttggc ctgttatgtt     780
accctcaatc gggtaaacaa cgtgatttcc aagattggcg aaattggtcc caaggatttt     840
ggcaaagtga tgggccttac agttcaggat atactggaag aaacgtcacg tgaaggcatt     900
actctgactc aagccgataa ccctagcctg atcaaaaagg aattagtcaa aatggtgcaa     960
gatgtcttgc gaccagcgtg gattgagcta gtcagt                              996
```

<210> SEQ ID NO 5
<211> LENGTH: 990
<212> TYPE: DNA
<213> ORGANISM: Artificial Sequence
<220> FEATURE:
<223> OTHER INFORMATION: Nucleotide sequence encoding ligase mutant

<400> SEQUENCE: 5

```
atgtttaaaa agtacagttc cctggaaaac cactacaact ctaagttcat cgagaaactg      60
tatagccttg gactgacttc tggtgaatgg gttgctcggg agaaaattca tggcaccaac     120
ttctcccctga ttattgagcg cgataaagtc acgtgtgcaa acgcacagg tccgatactt     180
cctgccgaag atttctatgg ctacgagatc atcatgaaaa agtacgacga tgcgatcaaa     240
gccgtgcagg atattatgga dacaagcgca gcagtgagtt atcaggtctt ggcgaatttt     300
gcgggtggag gaatccagaa aggggtagat tatggcgaca aagacttcta tgtctttgac     360
atcatcgtta ctacggaaga tggcgaagtt tcgtacatgg atgattacga gatggaatcc     420
ttctgtaaca cctttgggtt caaaatggct ccgttattag gtcgtggtag ctttgaggat     480
ctgattaaac tcccaaacga cttggatagc gtagtgaatg actataacgt gaccgtggat     540
gcggatctag tggaagccaa caaatgcgtg tttgatgcgg aagccaaagg cgaaaacacg     600
gctgaaggct atgtcctcaa gccatgctat ccgaaatggt tgcccaatgg caatcgagtg     660
gcaattaagt gcaaaaattc gaaatttagc gaaaagaaaa aaagcgataa gcctatcaaa     720
```

-continued

```
gcgaaagtag agctgtcaga agccgataat gacttggttg gtattctggc cgagtatgtt    780
acctggaatc gcgtgtctaa cgttatctcg aaaattgggg aagtaggtcc gaaagacttt    840
ggcaaagtta tgggcttaac cgtccaagac atactggaag aagcgtcacg tgaaggtatt    900
accctgaccc aagcggaaaa tccgagtctg gtgaagaaag aactcgtcaa atggtgatg     960 gatacgctgc gtgaagcgtg gattgaactg                                     990
```

<210> SEQ ID NO 6
<211> LENGTH: 996
<212> TYPE: DNA
<213> ORGANISM: Artificial Sequence
<220> FEATURE:
<223> OTHER INFORMATION: Nucleotide sequence encoding ligase mutant

<400> SEQUENCE: 6

```
atgttcaaga aatatagcag cctcgagaat cactacaact ctaagttcat agagaaactg     60
tattctctgg gactcacagg tggtgaatgg gtagctcggg agaaaatcca tggcacgaat    120
ttttcgctga tcatttccga tgataaagtc acctgtgcaa aacgcagtgg tccaatactt    180
ccagcagagg acttttttgg gtacgaaatc atcgtcaaaa attacgccga tgcgattcga    240
gcagtccaag acattatgga aactagtgcg gttgtttcgt atcaggtgtt cggtgagttt    300
gccggacctg gcattcagaa aaacgtcgac tatggcgata agacttcta cgtgtttgat    360 atcattgtta ccacggaatc cggagatgtc acctatgtag atgactacat gatggagagc    420
ttctgcaata cgttcaaatt caaaatggct ccgttgttag gtcgtgggaa atttgaagaa    480
ctgatcaaac tgccgaatga cctggatagt gtagtgaacg actacaactt taccgtggat    540
catgcgggct tagttgatgc caacaaatgc gtgtttaatg ccgaagcgaa aggcgaagtg    600
tttaccgctg aaggctatgt actgaaaccg tgttatccgt catggttgcg taacggtaat    660
cgtgtggcca ttaaatgcaa gaacagcaaa ttcagcgaga aaagaaatc cgataagcgc    720 atcaaagcga agtggaact gtctgaagcg gataacgagc ttgtaggcat tttagcgtgt    780
tatgtgactc taaatcgcgt gaacaacgtg atctcgaaaa ttggcgaagt tggccccaaa    840
gactttggga aagttatggg tctgacggtt caggacattc tggaagaagc ctcacgcgaa    900
ggtattacct tgacacaggc ggataattgg agcctgatta agaaggaact cgtcaaaatg    960
gtgcaagatg ttgtccgtga agcatggatc gaactg                              996
```

<210> SEQ ID NO 7
<211> LENGTH: 12
<212> TYPE: RNA
<213> ORGANISM: Artificial Sequence
<220> FEATURE:
<223> OTHER INFORMATION: Oligonucleotide

<400> SEQUENCE: 7

```
aacaguguuc uu                                                         12
```

<210> SEQ ID NO 8
<211> LENGTH: 13
<212> TYPE: RNA
<213> ORGANISM: Artificial Sequence
<220> FEATURE:
<223> OTHER INFORMATION: Oligonucleotide

<400> SEQUENCE: 8

```
uuauagagca aga                                                        13
```

```
<210> SEQ ID NO 9
<211> LENGTH: 10
<212> TYPE: RNA
<213> ORGANISM: Artificial Sequence
<220> FEATURE:
<223> OTHER INFORMATION: Oligonucleotide

<400> SEQUENCE: 9
acacuguuuu                                                          10

<210> SEQ ID NO 10
<211> LENGTH: 21
<212> TYPE: RNA
<213> ORGANISM: Artificial Sequence
<220> FEATURE:
<223> OTHER INFORMATION: Oligonucleotide

<400> SEQUENCE: 10
aacaguguuc uugcucuaua a                                             21

<210> SEQ ID NO 11
<211> LENGTH: 23
<212> TYPE: RNA
<213> ORGANISM: Artificial Sequence
<220> FEATURE:
<223> OTHER INFORMATION: Oligonucleotide

<400> SEQUENCE: 11
uuauagagca agaacacugu uuu                                           23

<210> SEQ ID NO 12
<211> LENGTH: 11
<212> TYPE: RNA
<213> ORGANISM: Artificial Sequence
<220> FEATURE:
<223> OTHER INFORMATION: Oligonucleotide

<400> SEQUENCE: 12
guaaccaaga g                                                        11

<210> SEQ ID NO 13
<211> LENGTH: 10
<212> TYPE: DNA
<213> ORGANISM: Artificial Sequence
<220> FEATURE:
<223> OTHER INFORMATION: Oligonucleotide

<400> SEQUENCE: 13
uauuccautt                                                          10

<210> SEQ ID NO 14
<211> LENGTH: 12
<212> TYPE: RNA
<213> ORGANISM: Artificial Sequence
<220> FEATURE:
<223> OTHER INFORMATION: Oligonucleotide

<400> SEQUENCE: 14
auggaauacu cu                                                       12

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide
```

```
<400> SEQUENCE: 15
guaaccaaga guauuccaut t                                            21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
auggaauacu cuugguuact t                                            21

<210> SEQ ID NO 17
<211> LENGTH: 12
<212> TYPE: RNA
<213> ORGANISM: Artificial Sequence
<220> FEATURE:
<223> OTHER INFORMATION: Oligonucleotide

<400> SEQUENCE: 17
aacaguguuc uu                                                      12

<210> SEQ ID NO 18
<211> LENGTH: 23
<212> TYPE: RNA
<213> ORGANISM: Artificial Sequence
<220> FEATURE:
<223> OTHER INFORMATION: Oligonucleotide

<400> SEQUENCE: 18
uuauagagca agaacacugu uuu                                          23

<210> SEQ ID NO 19
<211> LENGTH: 12
<212> TYPE: RNA
<213> ORGANISM: Artificial Sequence
<220> FEATURE:
<223> OTHER INFORMATION: Oligonucleotide

<400> SEQUENCE: 19
aacaguguuc uu                                                      12

<210> SEQ ID NO 20
<211> LENGTH: 12
<212> TYPE: RNA
<213> ORGANISM: Artificial Sequence
<220> FEATURE:
<223> OTHER INFORMATION: Oligonucleotide

<400> SEQUENCE: 20
aacaguguuc uu                                                      12

<210> SEQ ID NO 21
<211> LENGTH: 12
<212> TYPE: RNA
<213> ORGANISM: Artificial Sequence
<220> FEATURE:
<223> OTHER INFORMATION: Oligonucleotide

<400> SEQUENCE: 21
aacaguguuc uu                                                      12

<210> SEQ ID NO 22
```

```
<211> LENGTH: 12
<212> TYPE: DNA
<213> ORGANISM: Artificial Sequence
<220> FEATURE:
<223> OTHER INFORMATION: Oligonucleotide

<400> SEQUENCE: 22
aacaguguuc tu                                                            12

<210> SEQ ID NO 23
<211> LENGTH: 12
<212> TYPE: RNA
<213> ORGANISM: Artificial Sequence
<220> FEATURE:
<223> OTHER INFORMATION: Oligonucleotide

<400> SEQUENCE: 23
aacaguguuc uu                                                            12

<210> SEQ ID NO 24
<211> LENGTH: 12
<212> TYPE: RNA
<213> ORGANISM: Artificial Sequence
<220> FEATURE:
<223> OTHER INFORMATION: Oligonucleotide

<400> SEQUENCE: 24
aacaguguuc uu                                                            12

<210> SEQ ID NO 25
<211> LENGTH: 12
<212> TYPE: RNA
<213> ORGANISM: Artificial Sequence
<220> FEATURE:
<223> OTHER INFORMATION: Oligonucleotide

<400> SEQUENCE: 25
aacaguguuc uu                                                            12

<210> SEQ ID NO 26
<211> LENGTH: 12
<212> TYPE: DNA
<213> ORGANISM: Artificial Sequence
<220> FEATURE:
<223> OTHER INFORMATION: Oligonucleotide

<400> SEQUENCE: 26
aacaguguuc ut                                                            12

<210> SEQ ID NO 27
<211> LENGTH: 21
<212> TYPE: RNA
<213> ORGANISM: Artificial Sequence
<220> FEATURE:
<223> OTHER INFORMATION: Oligonucleotide

<400> SEQUENCE: 27
aacaguguuc uugcucuaua a                                                  21

<210> SEQ ID NO 28
<211> LENGTH: 13
<212> TYPE: RNA
<213> ORGANISM: Artificial Sequence
<220> FEATURE:
<223> OTHER INFORMATION: Oligonucleotide

<400> SEQUENCE: 28
```
uuauagagca aga 13

<210> SEQ ID NO 29
<211> LENGTH: 10
<212> TYPE: RNA
<213> ORGANISM: Artificial Sequence
<220> FEATURE:
<223> OTHER INFORMATION: Oligonucleotide

<400> SEQUENCE: 29
acacuguuuu 10

LIGASE MUTANT

CROSS REFERENCES TO RELATED APPLICATIONS

This application claims priority to Japanese Patent Application No. 2020-055033, filed on Mar. 25, 2020, and Japanese Patent Application No. 2021-010565, filed on Jan. 26, 2021, both of which are incorporated herein by reference in their entireties.

BACKGROUND OF THE INVENTION

Field of the Invention

The present invention relates to ligase mutants and the like.

Discussion of the Background

T4 RNA ligase 2 is an enzyme that is one type of RNA ligase (EC6.5.1.3) having an ability of linking ribonucleotides in the presence of ATP, and is derived from a T4 bacteriophage capable of infecting *Escherichia* (NP_049790). T4 RNA ligase 2 has an ability of forming a phosphodiester bond to link a phosphate group (donor) at the 5' end of a nucleic acid to a hydroxy group (acceptor) at the 3' end thereof. T4 RNA ligase 2 is used in a reaction such as linking overhanging double-stranded RNAs and linking nicks in double-stranded RNAs. T4 RNA ligase 2 is also known to be used for not only RNA but also DNA, and modified nucleic acids other than RNA and DNA as a substrate. Some mutants of T4 RNA ligase 2 are known.

For prior techniques for T4 RNA ligase 2, reference may be made to the following:

WO2008/094599;

INTERNET, NCBI Protein Database, Aug. 13, 2018, NP_049790, search date: Feb. 27, 2020.

Chauleau, M., & Shuman, S. (2013), Kinetic mechanism of nick sealing by T4 RNA ligase 2 and effects of 3'-OH base mispairs and damaged base lesions. RNA, 19 (12): 1840-1847;

Nandakumar, J., Shuman, S., Lima, C. D. (2006), RNA ligase structures reveal the basis for RNA specificity and conformational changes that drive ligation forward, Cell, 6; 127 (1): 71-84;

Ho, C. K., & Shuman, S. (2002), Bacteriophage T4 RNA ligase 2 (gp24.1) exemplifies a family of RNA ligases found in all phylogenetic domains. PNAS, 1; 99 (20): 12709-14;

Nandakumar, J., Ho, C. K., Lima, C. D., Shuman, S. (2004), RNA substrate specificity and structure-guided mutational analysis of bacteriophage T4 RNA ligase 2. J. Biol. Chem., 23; 279 (30): 31337-47;

Nandakumar, J. & Shuman, S. (2004), How an RNA ligase discriminates RNA versus DNA damage. Mol. Cell., 22; 16 (2): 211-21;

Nandakumar, J. & Shuman, S. (2005), Dual mechanisms whereby a broken RNA end assists the catalysis of its repair by T4 RNA ligase 2. J. Biol. Chem., 24; 280 (25): 23484-9;

Yin, S., Ho, C. K., Shuman, S. (2003), Structure-function analysis of T4 RNA ligase 2. J. Biol. Chem., 16; 278 (20): 17601-8; and Yin, S., Kiong Ho, C., Miller, E. S., Shuman, S. (2004), Characterization of bacteriophage KVP40 and T4 RNA ligase 2. Virology, 5; 319 (1): 141-51, all of which are incorporated herein by reference in their entireties.

SUMMARY OF THE INVENTION

Accordingly, it is one object of the present invention to provide novel ligase mutants having excellent properties.

It is another object of the present invention to provide novel methods for preparing such ligase mutants.

It is another object of the present invention to provide novel methods of using such ligase mutants.

These and other objects, which will become apparent during the following detailed description, have been achieved by the inventors' development of three types of ligase mutants Mut1 to 3 (SEQ ID NOs: 1 to 3) that show 93%, 87%, and 95% amino acid sequence identities, respectively, to T4 RNA ligase 2 (NP_049790) (see Table 1 as presented later) and have more excellent properties than those of the T4 RNA ligase 2. The aforementioned prior techniques do not teach or suggest such three types of ligase mutants.

That is, the present invention provides the following:

(1) A ligase mutant of the following (1), (2), or (3):

(1) a ligase mutant comprising an amino acid sequence showing 95% or more identity to the amino acid sequence of SEQ ID NO: 1, and having a nucleic acid-linking activity;

(2) a ligase mutant comprising an amino acid sequence showing 90% or more identity to the amino acid sequence of SEQ ID NO: 2, and having a nucleic acid-linking activity; or (3) a ligase mutant comprising an amino acid sequence showing 97% or more identity to the amino acid sequence of SEQ ID NO: 3, and having a nucleic acid-linking activity.

(2) The ligase mutant according to (1), wherein the nucleic acid is a single-stranded RNA or double-stranded RNA optionally containing DNA and/or a modified nucleic acid.

(3) A method for producing a nucleic acid product, the method comprising linking two or more nucleic acid materials in the presence of the ligase mutant according to claim 1 or 2 to form a nucleic acid product, wherein the two or more nucleic acid materials are selected from the group consisting of one or more single-stranded nucleic acid materials, one or more double-stranded nucleic acid materials, and a mixture thereof.

(4) The method according to (3), wherein the two or more nucleic acid materials are RNA.

(5) The method according to (3) or (4), wherein the two or more nucleic acid materials are four or more single-stranded RNAs.

(6) The method according to any of (3) to (5), wherein the nucleic acid product contains a complementary portion having a base length of 12 to 27.

(7) The method according to any of (3) to (6), wherein the two or more nucleic acid materials are DNA and/or a modified nucleic acid.

(8) The method according to any of (3) to (7), wherein the two or more nucleic acid materials have a concentration of 1 µM or more.

(9) The method according to any of (3) to (8), wherein the nucleic acid product is siRNA.

(10) A polynucleotide encoding the ligase mutant according to (1) or (2).

(11) An expression vector comprising the polynucleotide according to (10).

(12) A transformed microorganism comprising an expression unit comprising a polynucleotide encoding the ligase mutant according to (1) or (2), and a promoter operably linked to the polynucleotide.

(13) A method for producing a ligase mutant, the method comprising producing the ligase mutant according to (1) or (2) using the transformed microorganism according to (12).

According to the present invention, a nucleic acid product (e.g., a modified nucleic acid such as siRNA or a heteroduplex nucleic acid) can be efficiently produced from a nucleic acid material.

BRIEF DESCRIPTION OF THE DRAWINGS

FIG. 1 shows amino acid sequences (SEQ ID NOs: 1 to 3) of ligase mutants (Mut1 to 3) according to the present invention;

FIG. 2 shows a double-stranded oligonucleotide that is produced by a ligation reaction of four single-stranded oligonucleotide fragments, and the notation of a modified nucleotide residue is the same as that in Table 2;

FIG. 4A shows a double-stranded oligonucleotide that is produced by a ligation reaction of three single-stranded oligonucleotide fragments, and FIG. 4B shows graphs illustrating the amount of the double-stranded oligonucleotide (reaction time: 15 minutes). Oligonucleotide(s) in which a 2' position of a nucleotide residue positioned −2, −1, +1, or +2 from a ligation point is modified with a fluorine atom (F), O-methyl (Ome), or O-methoxyethyl (MOE), or substituted with a hydrogen atom (DNA) is used as a substrate.

DETAILED DESCRIPTION OF THE PREFERRED EMBODIMENTS

1. Ligase Mutant

Figure 3A:
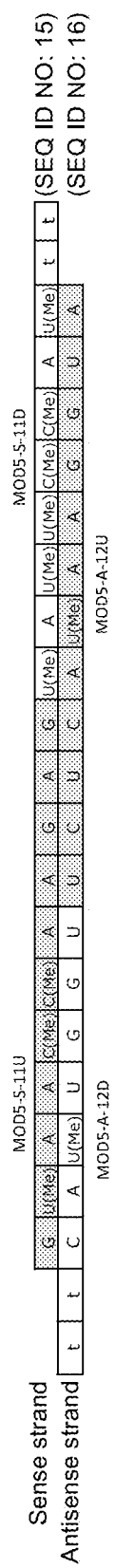
FIG. 3A shows a double-stranded oligonucleotide that is produced by a ligation reaction of four single-stranded oligonucleotide fragments.

The present invention provides a ligase mutant of the following (1), (2), or (3):

(1) a ligase mutant comprising an amino acid sequence showing 95% or more identity to the amino acid sequence of SEQ ID NO: 1, and having a nucleic acid-linking activity;

(2) a ligase mutant comprising an amino acid sequence showing 90% or more identity to the amino acid sequence of SEQ ID NO: 2, and having a nucleic acid-linking activity; or (3) a ligase mutant comprising an amino acid sequence showing 97% or more identity to the amino acid sequence of SEQ ID NO: 3, and having a nucleic acid-linking activity.

The amino acid sequence of SEQ ID NO: 1 shows 93% identity to the amino acid sequence of known T4 RNA ligase 2 (NP_049790). The ligase mutant of (1) is identified as an amino acid sequence showing 95% or more identity to the amino acid sequence of SEQ ID NO: 1, and therefore the ligase mutant is sufficiently distinguished from the known T4 RNA ligase 2. The percent identity to the amino acid sequence of SEQ ID NO: 1 in the ligase mutant of (1) may be preferably 96% or more, more preferably 97% or more, still more preferably 98% or more, and the most preferably 99% or more.

The amino acid sequence of SEQ ID NO: 2 shows 87% identity to the amino acid sequence of the known T4 RNA ligase 2 (NP_049790). The ligase mutant of (2) is identified as an amino acid sequence showing 90% or more identity to the amino acid sequence of SEQ ID NO: 2, and therefore the ligase mutant is sufficiently distinguished from the known T4 RNA ligase 2. The percent identity to the amino acid sequence of SEQ ID NO: 2 in the ligase mutant of (1) may be preferably 91% or more, more preferably 92% or more, still more preferably 93% or more, and the most preferably 94% or more, 95% or more, 96% or more, 97% or more, 98% or more, or 99% or more.

The amino acid sequence of SEQ ID NO: 3 shows 95% identity to the amino acid sequence of the known T4 RNA ligase 2 (NP_049790). The ligase mutant of (3) is identified as an amino acid sequence showing 97% or more identity to the amino acid sequence of SEQ ID NO: 3, and therefore the ligase mutant is sufficiently distinguished from the known T4 RNA ligase 2. The percent identity to the amino acid sequence of SEQ ID NO: 3 in the ligase mutant of (3) may be preferably 97.5% or more, more preferably 98% or more, still more preferably 98.5% or more, and the most preferably 99% or more or 99.5% or more.

The percent identity of an amino acid sequence can be calculated from a value that is obtained by executing Muscle alignment, ClustalW alignment, or Multiple sequence alignment for the full length of a polypeptide moiety encoded by ORF using software GENETYX Ver 13.1.1 manufactured by GENETYX CORPORATION, and executing calculation at a setting of Gaps are take into account. The number of modified amino acid residues (e.g., substituted, deleted, added or inserted amino acid residues or combination thereof) which can achieve the percent identity as described above to SEQ ID NO:1 (total length: 332 amino acid residues), SEQ ID NO:2 (total length: 330 amino acid residues), or SEQ ID NO:3 (total length: 332 amino acid residues) may be 1 to 33 for 90% or more, 1 to 29 for 91% or more, 1 to 26 for 92% or more, 1 to 23 for 93% or more, 1 to 19 for 94% or more, 1 to 16 for 95% or more, 1 to 13 for 96% or more, 1 to 9 for 97% or more, 1 to 6 for 98% or more, and 1 to 3 for 99% or more.

The ligase mutant according to the present invention has a nucleic acid-linking activity. Examples of the nucleic acid include a single-stranded nucleic acid and a double-stranded nucleic acid. In addition, examples of the nucleic acid include RNA, DNA, a modified nucleic acid other than RNA and DNA, and a nucleic acid mixture thereof. The nucleic acid may be preferably a single-stranded RNA or a double-stranded RNA that may contain DNA and/or a modified nucleic acid. Details of the nucleic acid are the same as those of a nucleic acid material in a method for producing a nucleic acid product described below.

The nucleic acid-linking activity of the ligase mutant according to the present invention is not particularly limited as long as it is more excellent than that of the T4 RNA ligase 2 (NP_049790). The ligase mutant may have a nucleic acid-linking activity that is preferably 1.2 or more times, more preferably 1.5 or more times, still more preferably 1.8 or more times, and particularly preferably 2.0 or more times that of the T4 RNA ligase 2. Such a nucleic acid-linking activity can be measured by a certain reaction as described in Examples. For example, such a reaction may be carried out in accordance with the following procedures a) to c) (for example, see Example 2):

a) 20 μL of reaction solution containing a nucleic acid material (for example, single-stranded RNA) in a final concentration of 10 μM, 50 mM Tris-HCl (pH: 7.5), 2 mM $MgCl_2$, 1 mM dithiothreitol, and 0.4 mM ATP is prepared;

b) to this reaction solution, 50 μL of purified ligase mutant-containing solution is added in a final concentration of 0.36 μg/mL, to initiate a reaction; and c) the reaction is carried out at 25° C. for 1 hour.

The ligase mutant according to the present invention may also have excellent temperature stability. For example, when a ligase mutant comprising amino acid sequences according to the present invention is subjected to a heat treatment, followed by measurement of activity, the ligase mutant preferably has a residual activity that is 30% or more, 40% or more, 50% or more, 60% or more, 70% or more, 80% or more, 90% or more, or 95% or more of the activity measured under a condition where the heat treatment is not carried out. Such a condition may be a condition where the temperature is kept at 25° C. for 23 hours, or the temperature is kept at 37° C. for 4 hours (for example, the temperature is kept in a solution containing 54 mM Tris-HCl (pH: 7.5), 2.2 mM $MgCl_2$, 1.1 mM dithiothreitol, 0.43 mM ATP, and 0.78 μg/mL of enzyme), and the activity is then measured. The measurement of activity may be carried out under a condition for a) to c) described in the aforementioned paragraph. Alternatively, the condition of measurement of activity may be a condition where the activity is measured in a reaction at 25° C. or 37° C. for 15 minutes. For example, a composition of a reaction solution used under such a condition may include 10 μM oligonucleotide, 50 mM Tris-HCl (pH: 7.5), 2 mM $MgCl_2$, 1 mM dithiothreitol, 0.4 mM ATP, and 0.72 μg/mL of enzyme. The temperature stability and liquid state stability and/or long-term storage stability of the enzyme may be generally interrelated, and therefore the ligase mutant according to the present invention that has excellent temperature stability can exhibit excellent liquid state stability and/or long-term storage stability. Accordingly, the ligase mutant according to the present invention is useful as a reagent.

The ligase mutant according to the present invention may have mutation at one or more amino acid residues as long as desired percent identity and linking activity are maintained. A position of an amino acid residue to which the mutation may be introduced is evident to a person skilled in the art. For example, a person skilled in the art can recognize correlativity between structures and functions by 1) comparing amino acid sequences of a plurality of proteins having a similar type of property (e.g., SEQ ID NOs: 1 to 3), 2) revealing relatively conserved regions and relatively not conserved regions, and then 3) predicting regions capable of playing a functionally important role and regions incapable of playing a functionally important role from the relatively conserved regions and the relatively not conserved regions, respectively. Therefore, a person skilled in the art can identify the position of the amino acid residue to which the mutation may be introduced in the amino acid sequence of the ligase mutant according to the present invention. An amino acid residue after mutation at such a position is a desired natural α-amino acid residue that is different from an amino acid residue before the mutation. Examples of such a desired natural α-amino acid residue include residues of L-alanine (A), L-aspartic acid (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), and glycine (G). In the amino acid residue showing 95% or more identity to the amino acid sequence of SEQ ID NO: 1, for example, 1 to 16 mutations of amino acid residues may be introduced to the amino acid sequence of SEQ ID NO: 1. In the amino acid residue showing 90% or more identity to the amino acid sequence of SEQ ID NO: 2, 1 to 33 mutations of amino acid residues may be introduced to the amino acid sequence of SEQ ID NO: 2. In the amino acid residue showing 97% or more identity to the amino acid sequence of SEQ ID NO: 3, 1 to 9 mutations of amino acid residues may be introduced to the amino acid sequence of SEQ ID NO: 3. The mutation of an amino acid residue is selected from the group consisting of substitution, deletion, addition, and insertion of the amino acid residue.

When an amino acid residue is mutated by substitution, the substitution of the amino acid residue may be conservative substitution. As used herein, the term "conservative substitution" refers to substitution of a certain amino acid residue with an amino acid residue having a similar side chain. Families of amino acid residues having the similar side chain are well-known in the art. Examples of such families include amino acids having a basic side chain (e.g., lysine, arginine, and histidine), amino acids having an acidic side chain (e.g., aspartic acid and glutamic acid), amino acids having an uncharged polar side chain (e.g., asparagine, glutamine, serine, threonine, tyrosine, and cysteine), amino acids having a non-polar side chain (e.g., glycine, alanine, valine, leucine, isoleucine, proline, phenylalanine, methionine, and tryptophan), amino acids having a position β branched side chain (e.g., threonine, valine, and isoleucine), amino acids having an aromatic side chain (e.g., tyrosine, phenylalanine, tryptophan, and histidine), amino acids having a hydroxy group (e.g., alcoholic or phenolic)-containing side chain (e.g., serine, threonine, and tyrosine), and amino acids having a sulfur-containing side chain (e.g., cysteine and methionine). Preferably, the conservative substitution of amino acid may be substitution between aspartic acid and glutamic acid, substitution between arginine, lysine and histidine, substitution between tryptophan and phenylalanine, substitution between phenylalanine and valine, substitution between leucine, isoleucine and alanine, or substitution between glycine and alanine.

The ligase mutant according to the present invention may also contain another peptide component (e.g., tag portion) on a C-terminal or an N-terminal. Examples of the other peptide component that may be contained in the ligase mutant according to the present invention include peptide components that make purification of a target protein easy (e.g., tag portions such as histidine tag and Strep-tag II; proteins generally used in purification of the target protein such as glutathione-S-transferase and maltose binding protein), peptide components that improve the solubility of the target protein (e.g., Nus-tag), peptide components that work as a chaperon (e.g., trigger factor), and peptide components that are a protein having another function or a domain of the protein or a linker for linking them to the ligase mutant.

2. Invention Involved in Production of Ligase Mutant of Invention

The ligase mutant according to the present invention can be prepared using a transformed microorganism comprising an expression unit comprising a polynucleotide encoding the ligase mutant according to the present invention and a promoter operably linked to the polynucleotide, or using a cell-free system, or the like. The present invention also provides such a polynucleotide and such a transformed microorganism, and an expression vector usable in production of the transformed product.

The polynucleotide according to the present invention is a polynucleotide encoding the ligase mutant according to the present invention. The polynucleotide according to the present invention may be DNA or RNA, and is preferably DNA.

For example, the transformed microorganism according to the present invention can be produced by a method using an expression vector comprising the polynucleotide according to the present invention (e.g., a competent cell method and an electroporation method) or genome modification technology. When the expression vector is an integrative vector that produces homologous recombination with genomic DNA of a host cell, an expression unit can be integrated into the genomic DNA of the host cell by transformation. On the other hand, when the expression vector is a non-integrative vector that does not produce homologous recombination with genomic DNA of a host cell, an expression unit is not integrated into the genomic DNA of the host cell by transformation, and can remain in the host cell in a state of the expression vector and exist independently from the genomic DNA. Alternatively, according to genome-editing technology (e.g., CRISPR/Cas System, Transcription Activator-Like Effector Nucleases (TALEN)), it is possible to integrate the expression unit into the genomic DNA of the host cell and to modify the expression unit inherently possessed by the host cell.

The present invention also provides an expression vector comprising the polynucleotide according to the present invention. The expression vector according to the present invention may further contain an element such as a terminator, a ribosome binding moiety, and a drug resistant gene that function in a host cell. Examples of the drug resistant gene include genes resistant to drugs such as tetracycline, ampicillin, kanamycin, hygromycin, and phosphinothricin.

The expression vector may also further contain a region capable of homologous recombination with genome DNA of a host cell for the homologous recombination with the genome DNA of the host cell. For example, the expression vector may be designed so that an expression unit contained therein is located between a pair of homologous regions (e.g., a homology arm homologous to a certain sequence in the genome of the host cell, loxP, and FRT). A genomic region (a target of a homologous region) of the host cell to which the expression unit is to be introduced is not particularly limited, and may be a locus of a gene expressed in a large amount in the host cell.

The expression vector may be a plasmid, a viral vector, a phage, or an artificial chromosome. The expression vector may also be an integrative vector or a non-integrative vector. The integrative vector may be a vector that is entirely integrated into a genome of a host cell. Alternatively, the integrative vector may be a vector, only a part (e.g., an expression unit) of which is integrated into the genome of the host cell. The expression vector may further be a DNA vector or an RNA vector (e.g., a retrovirus vector). The expression vector may also be a commonly used expression vector. Examples of such an expression vector include pUC (e.g., pUC19 and pUC18), pSTV, pBR (e.g., pBR322), pHSG (e.g., pHSG299, pHSG298, pHSG399, and pHSG398), RSF (e.g., RSF1010), pACYC (e.g., pACYC177 and pACYC184), pMW (e.g., pMW119, pMW118, pMW219, and pMW218), pQE (e.g., pQE30), and derivatives thereof.

As a host for expressing the ligase mutant according to the present invention, for example, various types of prokaryotic cells including bacteria in the genus *Escherichia* such as *Escherichia coli*, bacteria in the genus *Corynebacterium* (e.g., *Corynebacterium glutamicum*), and bacteria in the genus *Bacillus* (e.g., *Bacillus subtilis*), or various types of eukaryotic cells including bacteria in the genus *Saccharomyces* (e.g., *Saccharomyces cerevisiae*), bacteria in the genus *Pichia* (e.g., *Pichia stipitis*), and bacteria in the genus *Aspergillus* (e.g., *Aspergillus oryzae*) can be used. As the host, a strain in which a given gene is deleted may be used. Examples of the transformed microorganism include transformed microorganisms having an expression vector in a cytoplasm, and transformed microorganisms in which a target gene is introduced to a genome.

The transformed microorganism according to the present invention can be cultured, for example, in a culture medium having a composition described below by a certain culture device (e.g., a tube, a flask, and a jar fermenter). The culture condition can be appropriately set. Specifically, the culture temperature may be 10° C. to 37° C., the pH may be 6.5 to 7.5, and the culture time may be 1 hour to 100 hours. Culture may be carried out while the concentration of dissolved oxygen is controlled. In this case, the concentration of dissolved oxygen (DO value) in a culture broth may be used as an indication of control. Ventilating and agitating conditions can be controlled so that the concentration of dissolved oxygen DO value relative to an oxygen concentration in the air of 21% is not less than 1 to 10%, and preferably not less than 3% to 8%. The culture may be batch culture or fed-batch culture. In a case of fed-batch culture, a solution as a sugar source or a solution containing phosphoric acid is continuously or discontinuously, sequentially added to the culture broth. Thus, the culture can be continued.

A host to be transformed is as described above. *Escherichia coli* will be described in detail. *Escherichia coli* can be selected from *Escherichia coli* JM109, DH5α, HB101, and BL21(DE3) strains of subspecies of *Escherichia coli* K12 strain. A transformation method and a method for selecting a transformed microorganism are also described in Molecular Cloning: A Laboratory Manual, 3rd edition, Cold Spring Harbor press (2001 Jan. 15), which is incorporated herein by reference in its entirety, and the like. Hereinafter, a method in which transformed *Escherichia coli* is produced, and a certain enzyme is produced using the *Escherichia coli* will be specifically described as one example.

As a promoter for expressing the polynucleotide according to the present invention, a promoter generally used in production of a heteroprotein in *E. coli* can be used. Examples of the promoter include potent promoters such as PhoA, PhoC, a T7 promoter, a lac promoter, a trp promoter, a trc promoter, a tac promoter, and a PR promoter, a PL promoter, and a T5 promoter of phage lambda. PhoA, PhoC, and lac promoters are preferred. As a vector, for example, pUC (e.g., pUC19 and pUC18), pSTV, pBR (e.g., pBR322), pHSG (e.g., pHSG299, pHSG298, pHSG399, and pHSG398), RSF (e.g., RSF1010), pACYC (e.g., pACYC177 and pACYC184), pMW (e.g., pMW119, pMW118, pMW219, and pMW218), pQE (e.g., pQE30), or derivatives thereof may be used. As another vector, a vector of phage DNA may be used. Furthermore, an expression vector comprising a promoter and capable of expressing an inserted DNA sequence may be used. The vector may be preferably pUC, pSTV, or pMW.

A terminator that is a transcription termination sequence may be connected to a downstream of the polynucleotide according to the present invention. Examples of such a terminator include a T7 terminator, a fd phage terminator, a T4 terminator, a terminator of a gene resistance to tetracycline, and a terminator of trpA gene of *Escherichia coli*.

It is preferable that a vector for introducing the polynucleotide according to the present invention to *Escherichia coli* be so-called a multicopy vector. Examples of the vector include a plasmid having a replication origin derived from ColE1, for example, a pUC-based plasmid and a pBR322-based plasmid, or derivatives thereof. Herein, the term "derivative" means one obtained by modifying a plasmid by substitution, deletion, insertion, and/or addition of a base, or the like.

To select the transformed microorganism, it is preferable that the vector have a marker such as an ampicillin resistant gene. As such a plasmid, an expression vector having a potent promoter is commercially available (e.g., pUC-based (available from Takara Bio Inc.), pPROK-based (available from Clontech), and pKK233-2 (available from Clontech)).

The ligase mutant according to the present invention can be obtained by transforming *Escherichia coli* using an obtained expression vector according to the present invention, and culturing the *Escherichia coli*.

As the culture medium, a culture medium usually used for culture of *Escherichia coli*, such as a M9-casamino acid medium and a LB medium may be used. The culture medium may contain certain carbon source, nitrogen source, and coenzyme (e.g., pyridoxine hydrochloride). Specifically, peptone, a yeast extract, NaCl, glucose, $MgSO_4$, ammonium sulfate, potassium dihydrogen phosphate, ferric sulfate, manganese sulfate, or the like may be used. The culture condition and the production induction condition are appropriately selected depending on types of a marker of the used vector, the promoter, the host bacterium, and the like.

For collection of the ligase mutant according to the present invention, the following methods are exemplified. The ligase mutant according to the present invention can be obtained as a disrupted substance and a dissolved substance by collecting the transformed microorganism according to the present invention, and disrupting (e.g., sonication and homogenization) or dissolving (e.g., lysozyme treatment) bacterial cells. The ligase mutant according to the present invention can be obtained by performing a treatment, such as extraction, precipitation, filtration, and column chromatography, of the disrupted substance and the dissolved substance.

3. Method for Producing Nucleic Acid Product

The present invention also provides a method for producing a nucleic acid product including linking a nucleic acid material in the presence of the ligase mutant according to the present invention to produce a nucleic acid product. As the nucleic acid material, a material selected from the group consisting of a single-stranded nucleic acid material, a double-stranded nucleic acid material, and a mixture thereof can be used.

Nucleic Acid

A nucleic acid in the nucleic acid material and the nucleic acid product can be classified into a natural nucleic acid and a modified nucleic acid. A natural nucleic acid means a nucleic acid (RNA and DNA) including a nucleotide residue (adenosine (A), guanosine (G), cytidine (C), uridine (U), deoxyadenosine (dA), deoxyguanosine (dG), deoxycytidine (dC), or thymidine (dT), hereinafter referred to as "natural nucleotide residue") included in a polynucleotide contained in a cell. A modified nucleic acid is a nucleic acid other than the natural nucleic acid, which is a nucleic acid comprising a nucleotide residue other than the natural nucleotide residue (hereinafter referred to as "modified residue"). Examples of the modified residue include a modified nucleotide residue, an amino acid residue, and a linker. Examples of the modified nucleotide residue include a nucleotide residue having modification described below. An amino acid includes a derivative of the amino acid. Examples of the amino acid include glycine, alanine, valine, leucine, isoleucine, proline, methionine, phenylalanine, tryptophan, serine, threonine, asparagine, glutamine, tyrosine, cysteine, aspartic acid, glutamic acid, histidine, lysine, arginine, and derivatives thereof. The derivative of an amino acid means an amino acid in which any atom or group in the amino acid is substituted with another atom or group. Examples thereof include amino acids in which a hydrogen atom in an amino group, a hydrogen atom or an oxygen atom in a carboxy group, a hydroxy group, any atom or group in a side chain, or a hydrogen atom bonded to a skeleton carbon atom (e.g., α-, β-, γ-, and δ-carbon atoms) is substituted with another atom (e.g., a halogen atom such as a fluorine atom, a chlorine atom, a bromine atom, or an iodine atom) or group (e.g., a substituent after substitution in chemical modification described below).

Modification in the modified nucleotide residue includes substitution of an atom or group in a sugar moiety (ribose or deoxyribose) of the nucleotide residue, substitution of a sugar moiety (sugar skeleton) of the nucleotide residue, and modification of a nucleic acid base moiety of the nucleotide residue (e.g., substitution of a substituent of the nucleic acid base).

Examples of the substitution of an atom or group in the sugar moiety of the nucleotide residue include substitution of 1'-H, 2'-OH (only ribose), 2'-H, 3'-OH, 3'-$NH_2$, 3'-H, 3'-phosphate group, 4'-H, 5'-phosphate group, or a combination thereof. Herein, a phosphate group includes not only —O—P(O) $(OH)_2$, but also a group in which an oxygen atom is substituted with a sulfur atom or NH (e.g., —O—P(S) $(OH)_2$, —NH—P(O) $(OH)_2$, and —NH—P(S) $(OH)_2$). Furthermore, the phosphate group also includes a group (e.g., a protected phosphate group) in which a hydroxy group (—OH) is substituted with OR* (wherein R* is an organic group such as a protecting group of the phosphate group). Examples of such substitution include chemical modification of a 1', 2', 3', or 4' moiety (substitution at a 1', 2', 3', or 4' moiety with another substituent), modification of a 5'- or 3'-phosphate group (substitution of a 5'- or 3'-phosphate group with another substituent), bridging modification (substitution by bridging two of 1', 2', 3', and 4' moieties), and carrier-adding modification (substitution of a 1', 2', 3', 4', or 5' moiety with a carrier).

For example, chemical modification may be introduced to improve the degradation resistance of oligonucleotide. Examples of a substituent after substitution in the chemical modification include $C_{1-6}$ alkyloxy $C_{1-6}$ alkylene (e.g., methoxyethyl: MOE), —O—$C_{1-6}$ alkyl (e.g., —O-Me), —O—$C_{6-14}$ aryl (e.g., —O-phenyl), —C-aryl (e.g., —C-phenyl), a halogen atom (e.g., fluorine atom), —O—$C_{1-6}$ alkyl N-amide $C_{1-6}$ alkylene (e.g., —O—N-methylacetamide, —O-NMA), —O—$C_{1-6}$ alkyl-($C_{1-6}$ alkyl-)amino-$C_{1-6}$ alkylene (e.g., —O-dimethylaminoethoxyethyl, —O-DMAEOE), and —O-amino $C_{1-6}$ alkyl (e.g., —O-aminopropyl, —O-AP). The chemical modification is preferably chemical modification of a 2' moiety (substitution of a 2' moiety) or chemical modification of a 3' moiety (substitution of a 3' moiety), and more preferably chemical modification of a 2' moiety (substitution of a 2' moiety). Examples of a substituent after substitution in chemical modification of a 2' moiety include 2'-$C_{1-6}$ alkyloxy $C_{1-6}$ alkylene (e.g., 2'-methoxyethyl), 2'-O—$C_{1-6}$ alkyl (e.g., 2'-O-Me), 2'-O—$C_{6-14}$ aryl (e.g., 2'-O-phenyl), 2'-C-aryl (e.g., 2'-C-phenyl), a 2'-halogen atom (e.g., 2'-F), 2'-O—$C_{1-6}$ alkyl N-amide $C_{1-6}$ alkylene (e.g., 2'-O—N-methylacetamide, 2'-O-NMA), 2'-O—$C_{1-6}$ alkyl-($C_{1-6}$ alkyl)amino-$C_{1-6}$ alkylene (e.g., 2'-O-dimethylaminoethoxyethyl, 2'-O-

DMAEOE), and 2'-O-amino $C_{1-6}$ alkyl (e.g., 2'-O-aminopropyl, 2'-O-AP). Examples of a substituent after substitution in chemical modification of a 3' moiety include 3'-O—P(O) (OH)$_2$, 3'-O—P(S) (OH)$_2$, 3'-NH—P(O) (OH)$_2$, 3'-NH—P(S) (OH)$_2$), and a group in which a hydroxy group (—OH) in a phosphate group is substituted with OR* (wherein R* is an organic group such as a protecting group of the phosphate group described below).

For example, modification of a 5'- or 3'-phosphate group may be introduced to improve the degradation resistance of oligonucleotide. Examples of the modification of a 5'- or 3'-phosphate group include substitution from the phosphate group (—O—P(O) (OH)$_2$) to a group in which an oxygen atom in the phosphate group is substituted with a sulfur atom or NH. Examples of such a group include —O—P(S)(OH)$_2$ (thiophosphate group: phosphorothioate modification), —NH—P(O) (OH)$_2$, and —NH—P(S) (OH)$_2$. In the modification of a 5'- or 3'-phosphate group, a group (e.g., a protected phosphate group) in which a hydroxy group (—OH) in the phosphate group is substituted with OR* (wherein R* is an organic group such as a protecting group of the phosphate group) is also included. Examples of the protecting group of the phosphate group include a trityl (Tr) group, a p-methoxyphenyldiphenylmethyl (MMTr) group, a di(p-methoxyphenyl)phenylmethyl (DMTr) group, and a cyanoethyl group (CN—C$_2$H$_4$—).

For example, bridging modification may be introduced to improve the stereo structure stability of a nucleotide residue. Examples of the bridging modification include bridging modification of 2' and 4' moieties (substitution by bridging 2'-OH and 4'-H), and bridging modification of 3' and 5' moieties (substitution by bridging 3'-H and 5'-H). Examples of the bridging modification of 2' and 4' moieties include substitution of 2'-OH and 4'-H to 2'-O—C$_{1-6}$ alkylene-4' (e.g., substitution to 2'-O-methylene-4' (locked nucleic acid: LNA), 2'-O-ethylene-4' (ethylene-bridged nucleic acid: ENA), or 2'-O-methyl-substituted methylene-4' (constrained ethyl bridged nucleic acid: one type of BNA (cEt-BNA)), substitution of 2'-OH and 4'-H to 2'-O—C$_{1-6}$ alkylene-O—C$_{1-6}$ alkylene-4' (e.g., 2'-O-methylene-O-methylene-4' (bridged nucleic acid: one type of BNA (BNA$^{COC}$)), substitution of 2'-OH and 4'-H to 2'-O—N(R)—C$_{1-6}$ alkylene-4' (e.g., 2'-O—N(R)-methylene-4' (bridged nucleic acid: one type of BNA (BNA$^{NC}$), wherein R is methyl, a hydrogen atom, or benzyl), substitution of 2'-NH$_2$ and 4'-H to 2'-N (R)—C(O)-4' (e.g., 2'-N(methyl)—C(O)-4' (amido-bridged nucleic acid: AmNA)), substitution of 2'-NH$_2$ and 4'-H to 2'-NH—C$_{1-6}$ alkylene-4' (e.g., 2'-NH-methylene-4'), and substitution of 2'-H and 4'-H to 2'-C$_{1-6}$ alkylene-4' (e.g., 2'-methyl-substituted ethylene-4'). Examples of the bridging modification of 3' and 5' moieties include substitution of 3'-H and 5'-H to 3'-C$_{1-6}$ alkylene-5' (e.g., 3'-ethylene-5' (bicyclo nucleic acid: Bc nucleic acid), one type of Bc nucleic acid: tc nucleic acid).

A carrier in carrier-adding modification may be a carrier that improves performances such as stability, target directionality, and drug efficacy, or imparts the performances to a target modified oligonucleotide. Such a carrier can be appropriately selected from known carriers depending on the purposes of use. Examples of the carrier include N-acetyl galactosamine (GalNAc), peptide, phosphoric acid, cholesterol, tocopherol, aliphatic chain, and folic acid. An addition moiety in the carrier-adding modification is preferably a 3' or 5' moiety corresponding to a terminal of the target modified oligonucleotide.

Examples of a nucleotide residue having substitution of a sugar moiety of the nucleotide residue include a modified nucleotide residue having substitution from a sugar with a five-membered ring to a pseudo-sugar with a six-membered ring. Examples of such a modified nucleotide residue include a hexitol nucleic acid (HNA), and a cyclohexenyl nucleic acid (CeNA). Examples of the modified nucleotide residue having substitution of a sugar moiety of a nucleotide residue include a morpholino nucleic acid (PMO) residue that is an artificial compound of nucleotide analogue having a morpholino ring structure that is not degraded by an enzyme (e.g., nuclease such as RNase) in the living body and does not introduce an immune response.

Examples of modification of a nucleic acid base moiety of a nucleotide residue include alkyl substitution of the nucleic acid base moiety of the nucleotide residue (e.g., substitution at 5 position of a cytosyl group with a methyl group).

Nucleic Acid Material

The nucleic acid material may be a single nucleic acid material or a plurality of nucleic acid materials. For example, when an overhanging double-stranded nucleic acid is used as a single nucleic acid material, the method according to the present invention can be used for cyclization of the double-stranded nucleic acid. When a plurality of nucleic acid materials are used, the method according to the present invention can be used for linking including linking a plurality of overhanging double-stranded nucleic acids, linking a single overhanging double-stranded nucleic acid or a plurality of overhanging double-stranded nucleic acids to a single single-stranded nucleic acid or a plurality of single-stranded nucleic acids, and linking a plurality of single-stranded nucleic acids. When a plurality of nucleic acid materials are used, the number of the nucleic acid materials is not particularly limited as long as it is 2 or more. For example, the number may be as relatively small as 2 to 10, 2 to 8, 3 to 7, and 4 to 6, and may be more than 10.

The length of the nucleic acid material is not particularly limited. For example, a nucleic acid material having a base length of more than 1,000 can be used. Alternatively, when a short nucleic acid product is desired to be produced, a short nucleic acid material can be used. For example, the short nucleic acid material may have a base length of 5 or more, preferably 6 or more, more preferably 7 or more, still more preferably 8 or more, and particularly preferably 9 or more. The short nucleic acid material may have a base length of 19 or less, preferably 18 or less, more preferably 17 or less, still more preferably 16 or less, and particularly preferably 15 or less.

In the linking, an overhang may be used. Examples of an overhang used in the linking include an overhang in an overhanging double-stranded nucleic acid (nucleic acid material), and an overhang to be formed by annealing of nucleic acid materials (for example, a double-stranded nucleic acid and a single-stranded nucleic acid, or single-stranded nucleic acids). The length of the overhang is not particularly limited. When a short nucleic acid product is desired to be produced, for example, the overhang has a base length of 1 to 10, preferably 1 to 8, more preferably 1 to 6, and still more preferably 2 to 6, and may have a base length 3 to 6 or 4 to 6. Therefore, such an overhanging double-stranded nucleic acid, or a combination of a plurality of nucleic acid materials (for example, a combination of a double-stranded nucleic acid with a single-stranded nucleic acid, and a combination of a plurality of single-stranded nucleic acids) may be selected as the nucleic acid material.

The nucleic acid material may be in a free form, or may be fixed in a solid phase. When it is desired to complex the nucleic acid product with a functional portion, a corresponding portion of the nucleic acid material may be complexed with the functional portion.

The nucleic acid material can be produced by a chemical synthesis method (for example, a solid phase synthesis method and a liquid phase synthesis method) or an enzymatic synthesis method. Examples of the synthesis method include methods described in International publication WO2012/157723 and International publication WO2005/070859, both of which are incorporated herein by reference in their entireties.

The nucleic acid material may be preferably a single-stranded RNA or a double-stranded RNA that may contain DNA and/or a modified nucleic acid. Such a nucleic acid material may be more preferably the overhanging double-stranded RNA as described above, or a combination of a plurality of RNA materials to be formed by annealing (for example, a combination of a double-stranded RNA with a single-stranded RNA, and a combination of a plurality of single-stranded RNAs) as described above.

Nucleic Acid Product

The nucleic acid product contains a complementary portion in which bases are paired. Examples of such a nucleic acid product include a double-stranded nucleic acid, and a single-stranded nucleic acid containing a double-stranded-like structure moiety (e.g., a looped nucleic acid such as a hairpin-type nucleic acid or a dumbbell-type nucleic acid). The double-stranded nucleic acid may be a double-stranded nucleic acid in which each chain is the aforementioned nucleic acid. Examples of the double-stranded nucleic acid include a double-stranded RNA, a double-stranded DNA, a heteroduplex nucleic acid including RNA and DNA, a double-stranded nucleic acid including RNA and an RNA-DNA hybrid nucleic acid, a double-stranded nucleic acid including DNA and an RNA-DNA hybrid nucleic acid, and a double-stranded nucleic acid including RNA-DNA hybrid nucleic acids. Examples of the double-stranded nucleic acid include siRNA and a heteroduplex nucleic acid.

In a particular embodiment, the nucleic acid product may have the aforementioned modified residue at the complementary portion. Examples of such a nucleic acid product include a double-stranded nucleic acid or looped nucleic acid containing a modified nucleotide residue (for example, a double-stranded nucleic acid or looped nucleic acid containing a modified nucleotide residue at the complementary portion), and a looped nucleic acid containing a modified nucleotide residue or a residue other than a nucleotide residue (for example, an amino acid residue, a linker, or the like) at a loop moiety (for example, International publication WO2012/005368, which is incorporated herein by reference in its entirety). In such a nucleic acid product, a part of the nucleotide residue may be a modified nucleotide residue, or the whole of the nucleotide residue may be a modified nucleotide residue. When the modified nucleotide residue is a morpholino nucleic acid (PMO) residue, it is preferable that a part of the nucleotide residue in a target modified nucleic acid be a morpholino nucleic acid (PMO) residue. Such a nucleic acid product contains a gapmer that is a nucleic acid having the modified nucleotide residue at both ends of a sequence thereof and a gap region for receiving recognition of RNase at a center of the sequence. Furthermore, the nucleic acid product contains a nucleic acid that does not introduce RNase activity, such as a mixmer that is a nucleic acid having the modified nucleotide residue on the sequence, and a fully modified nucleic acid that is a nucleic acid in which all nucleotide residues in the sequence are a modified nucleotide residue.

The nucleic acid product may be a nucleic acid including only the complementary portion in which bases are paired. In addition to the complementary portion, the nucleic acid product may be a nucleic acid including a noncomplementary portion in which bases are not paired. The length of the complementary portion and/or the noncomplementary portion is not particularly limited. The complementary portion and/or the noncomplementary portion may be short. For example, a short complementary portion may have a base length 11 to 27, 12 to 27, 15 to 27, or 18 to 27. For example, a short noncomplementary portion may have a base length of 1 to 16, 1 to 10, 1 to 5, or 1, 2, or 3. When the nucleic acid product has the noncomplementary portion in addition to the complementary portion, the complementary portion may have a continuous form, or a discontinuous form in which the nucleic acid product is divided by the noncomplementary portion. The length of the nucleic acid product is not particularly limited, and the nucleic acid product may be short. For example, a short nucleic acid product may have a base length of 20 to 80, or 24 to 74.

The nucleic acid product may be preferably a single-stranded RNA or a double-stranded RNA that may contain DNA and/or a modified nucleic acid. The nucleic acid product may more preferably have the aforementioned modified residue at the complementary portion.

Reaction Condition for Linking

As a reaction system, an aqueous solution can be used. The aqueous solution is preferably a buffer. Examples of the buffer include a phosphate buffer, a Tris buffer, a carbonate buffer, an acetate buffer, and a citrate buffer. For example, the pH may be about 5 to 9. For example, when efficient mass production of a target nucleic acid product is particularly desired, the pH may be 7.5 to 9.0 (for example, 8.0 to 8.5).

The concentration of each nucleic acid material in a linking reaction may be a concentration sufficient to dissolve the nucleic acid materials and produce the target nucleic acid product. For example, the concentration of each nucleic acid material may be 1 µM or more, 10 µM or more, 50 µM or more, 100 µM or more, 300 µM or more, 500 µM or more, or 1,000 µM or more. For example, the concentration of each nucleic acid material may be 1 M, 100 mM, or 10 mM or less. When efficient mass production of the target nucleic acid product is particularly desired, it is preferable that each nucleic acid material in a concentration of 100 µM or more of the aforementioned concentrations be used.

When a plurality of nucleic acid materials are used in the linking reaction, it is preferable that the numbers of moles of all the nucleic acid materials be approximately equal to each other from the viewpoint of decreasing the amounts of nucleic acid materials unreacted to improve production efficiency. To make the numbers of moles of all the nucleic acid materials approximately equal, the molar ratio of any two selected from the nucleic acid materials may fall within a range of, for example, 0.5 to 2, preferably 1/1.8 to 1.8, more preferably 1/1.5 to 1.5, still more preferably 1/1.2 to 1.2, and particularly preferably 1/1.1 to 1.1.

The concentration of the ligase mutant according to the present invention in the linking reaction may be a concentration sufficient to produce the target nucleic acid product. The concentration of the ligase mutant may be, for example, 0.01 U/µL or more, preferably 0.02 U/µL or more, more preferably 0.03 U/µL or more, and still more preferably 0.04 U/µL or more. For example, the concentration of the ligase mutant may be 1 U/µL or less, preferably 0.5 U/µL or less, more preferably 0.2 U/µL or less, and still more preferably 0.1 U/µL or less. Herein, 1 unit (U) is defined as the enzyme amount required for production of 1 μmol of nucleic acid product for 1 hour in a reaction described in Example 2.

The reaction system may contain a cofactor. Examples of the cofactor include ATP and a divalent metal salt (e.g., a magnesium salt such as magnesium chloride). The reaction system may contain a stabilizer for a ligase. Examples of the stabilizer for a ligase include an antioxidant (e.g., reductants such as dithiothreitol and mercaptoethanol). The reaction system may contain a surfactant for stable retention of an enzyme and an increase in reaction rate. Examples of the surfactant include a nonionic surfactant (e.g., Triton series surfactants such as Triton X-100) and an ionic surfactant. Examples of the ionic surfactant include a cationic surfactant, an anionic surfactant, and an amphoteric surfactant). The reaction system may contain polyethylene glycol for an increase in reaction rate, and the like The reaction system may contain a low concentration of univalent cation salt or may not substantially contain a univalent cation salt. When the reaction system contains a univalent cation salt, the concentration of the univalent cation salt in the reaction system may be, for example, 10 mM or less, preferably 1 mM or less, more preferably 0.1 mM or less, and still more preferably 0.01 mM or less. It is particularly preferable that the reaction system does not substantially contain the univalent cation salt. Examples of the univalent cation salt include salts of univalent cations such as a lithium ion, a sodium ion, a potassium ion, a rubidium ion, a cesium ion, and an ammonium ion with anions such as a fluoride ion, a chloride ion, a bromide ion, and an iodide ion.

The reaction temperature may be a temperature sufficient for activation of the ligase mutant according to the present invention. Such a temperature may be, for example, 2 to 50° C., preferably 16 to 50° C., and more preferably 25 to 50° C.

The reaction time may be a time sufficient to produce the target nucleic acid product. For example, such a time may be 1 to 72 hours.

Other features of the invention will become apparent in the course of the following descriptions of exemplary embodiments which are given for illustration of the invention and are not intended to be limiting thereof.

EXAMPLES

Example 1: Design and Preparation of RNA Ligase

1) Design of RNA Ligase 425 similar sequences were obtained by Blastp using T4 RNA ligase 2 (NP_049790.1) having a known function as a template. As an analysis condition of Blastp, a value of Max target sequences was set to 10,000, and a value of Expected threshold was set to $1.0E^{-6}$. The obtained similar sequences were analyzed, and duplicated sequences and sequences having a sequence length that was clearly different from that of the template were removed to select 172 of the sequences. Thus, a sequence library was formed. By applying a procedure used in Nakano, S., Motoyama, T., Miyashita, Y., Ishizuka, Y., Matsuo, N., Tokiwa, H., Shinoda, S., Asano, Y., and Ito, S. (2018) Benchmark Analysis of Native and Artificial $NAD^+$-Dependent Enzymes Generated by a Sequence-Based Design Method with or without Phylogenetic Data, Biochemistry 57, 3722-3732, and Nakano, S., Niwa, M., Asano, Y., and Ito, S. (2019) Following the Evolutionary Track of a Highly Specific 1-Arginine Oxidase by Reconstruction and Biochemical Analysis of Ancestral and Native Enzymes, Appl Environ Microbiol 85, e00459-00419, both of which are incorporated herein by reference in their entireties, a motif-like sequence of T4 RNA ligase 2 (Ala at 32 position, Phe at 116 position, Ser at 170 position, and Ile at 274 position) was identified. From the sequence library, only a sequence having the motif-like sequence was selected. Finally, data on 21 of the sequences were obtained. Using the 21 sequences, artificial design was carried out. Artificial RNA ligase sequences represented by amino acid sequences of SEQ ID NOs: 1 to 3, named Mut1, Mut2, and Mut3, were designed (see FIG. 1).

TABLE 1

| Amino acid sequence identity (%) to T4 RNA ligase 2 (NP_049790) | |
|---|---|
| | Identity (%) |
| Mut1 (SEQ ID NO: 1) | 93 |
| Mut2 (SEQ ID NO: 2) | 87 |
| Mut3 (SEQ ID NO: 3) | 95 |

2) Construction of Expression Strain of Artificial RNA Ligase

The designed RNA ligases were subjected to *Escherichia coli* codon-optimization, and expression plasmids linked to Nde I and Bam HI sites of pEt-16b (Merck Millipore) were synthesized by Eurofins Genomics K. K. The artificially designed RNA ligase expression plasmids having base sequences of SEQ ID NOs: 4 to 6 as ORF corresponding to Mut1, Mut2, and Mut3, respectively, were each transformed into an *Escherichia coli* BL21 (DE3) strain, applied to a LB agar plate containing 100 mg/L of ampicillin, and cultured at 37° C. overnight, to obtain colonies. The colonies were separated to obtain an expression strain of each of the RNA ligases. On the expression strains, each of RNA ligases having a His-tag at an N-terminal was expressed.

3) Expression of Artificial RNA Ligase

The expression strain of each of the RNA ligases was applied to a LB agar plate containing 100 mg/L of ampicillin, and cultured at 37° C. overnight. Grown bacterial cells were picked by an inoculating loop, and inoculated into a 500-mL Sakaguchi flask containing 150 mL of a LB culture medium containing 100 mg/L of ampicillin. The bacterial cells were subjected to shake culture at 37° C. and 120 rpm for 3 hours until $OD_{600}$ was 0.5, isopropyl β-D-1-thiogalactopyranoside (IPTG) was added in a final concentration of 0.1 mM, and culture was continued at 37° C. and 120 rpm for 3 hours. After completion of the culture, the bacterial cells were collected from 150 mL of the resulting culture broth by centrifugation at 8,000 rpm for 30 minutes.

4) Purification of RNA Ligase

The collected bacterial cells were suspended in 15 mL of 50 mM tris(hydroxymethyl)aminomethane-HCl buffer (pH: 7.5) containing 250 mM NaCl, 10% sucrose, and 15 mM imidazole. Furthermore, lysozyme (Sigma-Aldrich) in a final concentration of 50 μg/mL and 10% Triton-X100 in a final concentration of 0.1% were added, and the mixture was left to stand on ice for 30 minutes. After 30 minutes, the bacterial cells were lysed by an ultrasonic crusher (Insonator 201M) (KUBOTA Corporation). Cell debris was removed by centrifugation at 10,000×g for 10 minutes, to obtain a supernatant as a soluble fraction.

The obtained soluble fraction was added to and adsorbed on HisTALON Superflow Cartridge (5 mL) (Takara Bio Inc.) equilibrated by the buffer using AKTA Pure (GE Healthcare Life Sciences). An unadsorbed protein was cleaned with 30 mL of Tris-HCl buffer (pH: 7.5) buffer containing 250 mM NaCl, 10% sucrose, and 15 mM imidazole, and then eluted in 50 mM Tris-HCl (pH: 8.0) buffer containing 250 mM NaCl, 10% glycerol, and 200 mM imidazole.

The elution of the protein was detected by absorption at 280 nm, and an RNA ligase-containing fraction expressed as a His-tag fused protein was collected. 4 mL of the eluted fraction was concentrated using Amicon Ultra-15 10 kDa (Merck Millipore), and the buffer was replaced by 10 mM Tris-HCl (pH: 7.5) buffer containing 50 mM KCl, 35 mM $(NH_4)_2SO_4$, 0.1 mM EDTA, 0.1 mM DTT, and 50% glycerol, to obtain 50 µL of solution. The purified enzyme was stored at −20° C. in this buffer solution form. The artificial RNA ligases having amino acid sequences of SEQ ID NOs: 1 to 3 were named Mut1, Mut2, and Mut3, respectively. From 150 mL of the culture broth, 4.2 mg of the artificial RNA ligase Mut1, 1.1 mg of the artificial RNA ligase Mut2, and 0.65 mg of the artificial RNA ligase Mut3 were each obtained.

Example 2: Ligation Reaction of Four Fragments Using Each Artificial RNA Ligase

1) RNA Ligation Reaction Condition

Figure 2:
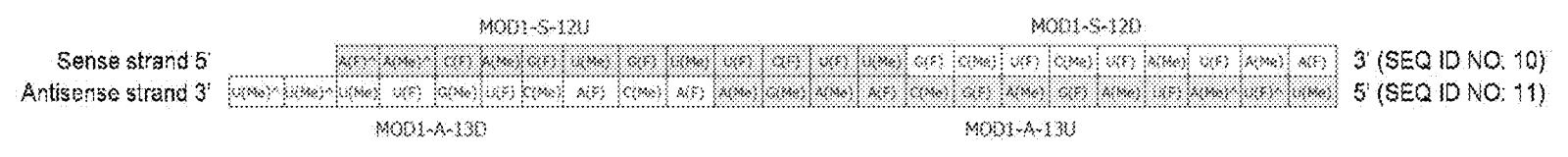

The ligase activities of three types of the prepared artificial RNA ligases were measured under the following condition. A reaction in which four oligonucleotide fragments in Table 2 were used as substrates, and linked as illustrated in FIG. 2, to produce two complemented nucleotide fragments was carried out. Commercially available T4 RNA ligase 2 (New England Biolabs) was used as a control. For the sake of convenience, an oligonucleotide produced by a linking reaction of MOD1-S-12U and MOD1-S-12D was referred to as a sense strand, and an oligonucleotide produced by a linking reaction of MOD1-A-13U and MOD1-A-13D was referred to as an anti-sense strand.

20 µL of reaction solution containing the respective oligonucleotides in a final concentration of 10 µM, 50 mM Tris-HCl (pH: 7.5), 2 mM $MgCl_2$, 1 mM dithiothreitol, and 0.4 mM ATP was prepared on ice, and placed into a 200-µL microtube, and 50 µL of each of the purified enzyme solutions in a final concentration of 0.36 µg/mL was added to initiate the reaction. The reaction solution was warmed at 25° C. by a thermal cycler, the temperature was increased to 80° C. 1 hour after the initiation of the reaction, and the reaction solution was heated for 5 minutes, to terminate the reaction. The concentration of each ligation product was determined by HPLC under the following condition.

TABLE 2

Oligonucleotide using ligation reaction of four fragments

| Fragment | Name | Sequence | SEQ ID NO |
|---|---|---|---|
| Sense strand, 5'-end | MOD1-S-12U | A(F)^A(Me)^C(F)A(Me)G(F)U(Me)G(F)U(Me)U(F)C(F)U(F)U(Me) | 7 |
| Sense strand, 3'-end | MOD1-S-12DPho- | G(F)C(Me)U(F)C(Me)U(F)A(Me)U(F)A(Me)A(F) | — |
| Antisense strand, 5'-end | MOD1-A-13U | U(Me)^U(F)^A(Me)U(F)A(Me)G(F)A(Me)G(F)C(Me)A(F)A(Me)G(Me)A(Me) | 8 |

TABLE 2-continued

Oligonucleotide using ligation reaction of four fragments

| Fragment | Name | Sequence | SEQ ID NO |
|---|---|---|---|
| Antisense strand, 3'-end | MOD1-A-13DPho- | A(F)C(Me)A(F)C(Me)U(F)G(Me)U(F)U(Me)^U(Me)^U(Me) | 9 |

Pho: Modification of 5'-end with a phosphate group
(F): Modification with 2'-fluoro group
(Me): Modification with 2'-O-methyl group
^Replacement of a phosphate group with a thiophosphate group 2) Analysis by HPLC The oligonucleotides as the ligation products were subjected to quantitative determination by HPLC using ACQUITY UPLC (registered trademark) Oligonucleotide BEH C18 Column (Waters, 1.7 µm 2.1×50 mm). Analysis was carried out by HPLC under a condition including a column temperature of 60° C., a detection wavelength of 260 nm, an injection amount of 10 µL, and a flow rate of 0.4 mL/min, and a linear gradient listed in Table 3 using an eluent A containing 100 mM hexafluoroisopropanol, 8 mM triethylamine, and 0.004% phosphoric acid, and an eluent B containing 10% methanol as mobile phases. An oligonucleotide having the same sequence as that of each of the products synthesized according to the ligations was separately synthesized. The concentration of each of the ligation products was determined using this oligonucleotide as an authentic sample.

TABLE 3

| Gradient condition | | | |
|---|---|---|---|
| Time (min) | A % | B % | Curve |
| 0.00 | 95 | 5 | — |
| 8.00 | 75 | 25 | 6 |
| 8.10 | 10 | 90 | 6 |
| 10.50 | 10 | 90 | 6 |
| 10.60 | 95 | 5 | 6 |
| 14.00 | 95 | 5 | 6 |

3) Results

Results are listed in Table 4. For the sake of convenience, the oligonucleotide produced by the linking reaction of MOD1-S-12U and MOD1-S-12D was referred to as a sense strand. By a reaction using T4 RNA ligase 2 as a control for 1 hour, 0.47 µM ligation product of the sense strand was produced. The reaction rates in the reactions using the artificial RNA ligases were increased. In the reaction using Mut1, 1.98 µM ligation product was produced, and the activity was largely increased about 4.2 times that in the reaction using T4 RNA ligase 2. In the reactions using Mut2 and Mut3, increased activities were observed, and the amounts of the ligation products obtained by the reactions for 1 hour were increased about 2.2 times that in the reaction using T4 RNA ligase 2. In these reactions, 1 unit (U) is defined as the enzyme amount required for production of 1 µmol of ligation product for 1 hour. In a case of using Mut1 having the highest activity, the activity was calculated to be 5.50 units/mg.

TABLE 4

Production amount and specific activity
in ligation using artificial RNA ligase

| Enzyme | Sense strand (μM) produced by reaction for 1 hour | Specific activity (unit/mg) |
|---|---|---|
| T4 RNA ligase2 (New England Biolabs) | 0.47 | 1.31 |
| Mut1 | 1.98 | 5.50 |
| Mut2 | 1.04 | 2.89 |
| Mut3 | 1.04 | 2.89 |

Example 3: Ligation Reaction of Four Fragments Using Each Artificial RNA Ligase Under Condition of High Concentration of Substrate The substrate concentration was increased, and a ligation reaction using the RNA ligase Mut1 having the highest activity was carried out. As substrates, four oligonucleotide fragments in Table 5 were used. A reaction was carried out using T4 RNA ligase 2 (New England Biolabs) as a control. As illustrated in FIG. 3A, an oligonucleotide produced by a linking reaction of MOD5-S-11U and MOD5-S-11D was referred to as a sense strand, and an oligonucleotide produced by a linking reaction of MOD5-A-12U and MODS-A-12D was referred to as an anti-sense strand.

10 μL of reaction solution containing the oligonucleotides in a final concentration of 500 μM, 50 mM Tris-HCl (pH: 8.0), 2 mM MgCl$_2$, 1 mM dithiothreitol, 1.4 mM ATP, and 7.2 μg/mL of each of the enzymes was placed into a 200-μL microtube, and warmed at 25° C. by a thermal cycler. 0.5, 1, 2, 4, 6, and 24 hours after initiation of the reaction, 1 μL of each of the reaction solutions was sampled, and 49 μL of 10 mM EDTA solution was added to terminate the reaction. The concentration of each ligation product was determined by HPLC under the condition described in Example 2.

Figure 3B:
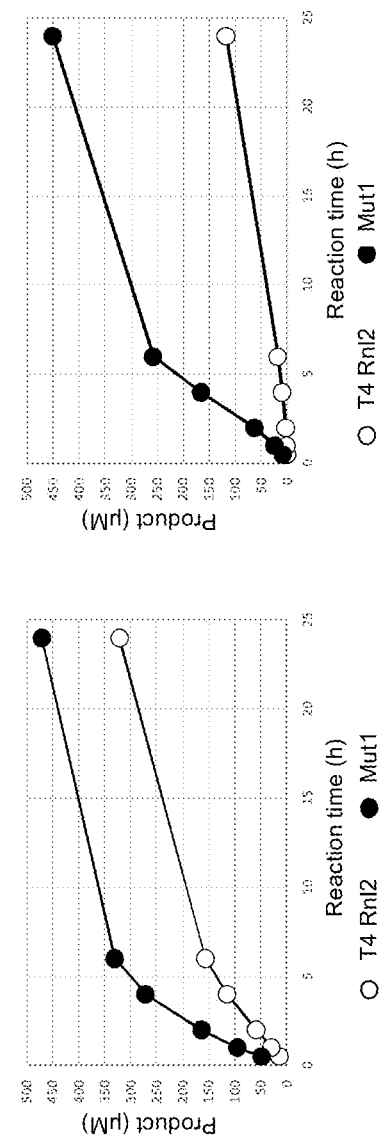
FIG. 3B shows graphs illustrating a time course of production of the double-stranded oligonucleotide, and the notation of a modified nucleotide residue is the same as that in Table 4.

Time courses of productions of the ligation products are illustrated in FIG. 3B. In the reaction using T4 RNA ligase 2 as a control, the production rate of the ligation product on an anti-sense strand side was slow, and the amounts of the ligation products of the anti-sense strand and the sense strand side 24 hours after the reaction were 320 μM and 120 μM, respectively. A part of the four oligonucleotide fragments added as the substrates remained unreacted.

On the other hand, in the reaction using Mut1 having improved ligation activity, the ligation rates of the oligonucleotides on the sense strand side and the anti-sense strand side were largely improved. The amounts of the ligation products on the anti-sense strand side and the sense strand side 24 hours after the reaction were 470 μM and 450 μM, respectively. The four oligonucleotide fragments added as the substrates were approximately completely consumed.

TABLE 5

Oligonucleotide used in ligation reaction of four fragments at high concentration

| Fragment | Name | Sequence | SEQ ID NO |
|---|---|---|---|
| Sense strand, 5'-end | MOD5-S-11U | GU(Me)AAC(Me)C(Me)AAGAG | 12 |
| Sense strand, 3'-end | MOD5-S-11D | Pho_U(Me)AU(Me)U(Me)(C(Me)CMe)AU(Me)tt | 13 |
| Antisense strand, 5'-end | MOD5-A-12U | AUGGAAU(Me)ACUCU | 14 |
| Antisense strand, 3'-end | MOD5-A-12D | Pho_UGGUU(Me)ACtt | — |

Pho: Modification of 5'-end with a phosphate group
(Me): Modification with 2'-O-methyl group
lower case letter: DNA

Example 4: Substrate Specificity of Artificial RNA Ligase

In a reaction for linking two oligonucleotide fragments using three oligonucleotide fragments as substrates as illustrated in FIG. 4A, a change of substrate specificity of the artificial RNA ligase was examined. An oligonucleotide in which the vicinity of ligation point of an oligonucleotide to be linked was substituted with modified RNA, specifically an oligonucleotide in which 2' position of a moiety positioned −2, −1, +1, or +2 from the ligation point was modified with a fluorine atom (F) or O-methyl or O-methoxyethyl, or substituted with a hydrogen atom (DNA) as listed in Table 6 was used as a substrate. The RNA ligase Mut1 having the highest activity and T4 RNA ligase 2 (New England Biolabs) as a control were used. 20 μL of reaction solution containing the oligonucleotides in a final concentration of 10 μM, 50 mM Tris-HCl (pH: 7.5), 2 mM MgCl$_2$, 1 mM dithiothreitol, 0.4 mM ATP, and 1.78 μg/mL of each of the enzymes was placed into a 200-μL microtube, and warmed at 25° C. 15 minutes after initiation of the reaction, 3 μL of each of the reaction solutions was sampled, and 27 μL of 10 mM EDTA solution was added to terminate the reaction. The concentrations of ligation products contained in the reaction solutions were determined by HPLC under the condition described in Example 2. Using a ligation product containing no modified nucleic acid as an authentic sample, the amounts of the products were determined.

The amounts of ligation products produced by the reaction for 15 minutes are illustrated in FIG. 4B. In a case of using T4 RNA ligase 2 as a control, the amount of the ligation product when the substrate was an oligonucleotide in which a −2 position was substituted with 2'-F, 2'-MOE, or DNA or a −1 position was substituted with 2'-O-Me, 2'-MOE, or DNA was largely decreased to 5 to 50%, as compared with a case where the substrate was a fragment including a natural RNA as a whole. On the other hand, in a case of using Mut1 having improved ligation activity, the amount of the ligation product when the substrate was an oligonucleotide in which a −2 position was substituted with 2'-F and DNA was substantively the same as that when the substrate was a fragment including a natural RNA as a whole. In the case of using Mut1, the amount of the ligation product was two or more times that in the case of using T4 RNA ligase 2 even when the substrate was any oligonucleotide.

TABLE 6

Oligonucleotide used in ligation reaction of three fragments

| Fragment | Name | Sequence | SEQ ID NO |
|---|---|---|---|
| Sense strand, 5'-end | RNA1-S-12U-H | AACAGUGUUCUU | 17 |
| Sense strand, 3'-end | RNA1-S-12D-H | Pho-GCUCUAUAA | — |
| Antisense strand | RNA1-A-H | UUAUAGAGCAAGAACACUGUUUU | 18 |
| Sense strand, 5'-end | RNA1-S-12U-F(-2)-H | AACAGUGUUCU(F)U | 19 |
| Sense strand, 5'-end | RNA1-S-12U-Ome(-2)-H | AACAGUGUUCU(Me)U | 20 |
| Sense strand, 5'-end | RNA1-S-12U-MOE(-2)-H | AACAGUGUUCU(m)U | 21 |
| Sense strand, 5'-end | RNA1-S-12U-dT(-2)-H | AACAGUGUUCtU | 22 |
| Sense strand, 5'-end | RNA1-S-12U-F(-1)-H | AACAGUGUUCUU(F) | 23 |
| Sense strand, 5'-end | RNA1-S-12U-Ome(-1)-H | AACAGUGUUCUU(Me) | 24 |
| Sense strand, 5'-end | RNA1-S-12U-MOE(-1)-H | AACAGUGUUCUU(m) | 25 |
| Sense strand, 5'-end | RNA1-S-12U-dT(-1)-H | AACAGUGUUCUt | 26 |
| Sense strand, 3'-end | RNA1-S-12D-F(+1)-H | Pho-G(F)CUCUAUAA | — |
| Sense strand, 3'-end | RNA1-S-12D-Ome(+1)-H | Pho-G(Me)CUCUAUAA | — |
| Sense strand, 3'-end | RNA1-S-12D-MOE(+1)-H | Pho-G(m)CUCUAUAA | — |
| Sense strand, 3'-end | RNA1-S-12D-dT(+1)-H | Pho-gCUCUAUAA | — |
| Sense strand, 3'-end | RNA1-S-12D-F(+2)-H | Pho-GC(F)UCUAUAA | — |
| Sense strand, 3'-end | RNA1-S-12D-Ome(+2)-H | Pho-GC(Me)UCUAUAA | — |
| Sense strand, 3'-end | RNA1-S-12D-MOE(+2)-H | Pho-GC(m)UCUAUAA | — |
| Sense strand, 3'-end | RNA1-S-12D-dT(+2)-H | Pho-GcUCUAUAA | — |

Pho: Modification of 5'-end with a phosphate group
(F): Modification with 2'-fluoro group
(Me): Modification with 2'-O-methyl group
(m): Modification with 2'-O-methoxyethyl group
lower case letter: DNA

Example 5: Temperature Stability of Artificial RNA Ligase

The temperature stability of the artificial RNA ligase was evaluated. The RNA ligase Mut1 having the highest activity and T4 RNA ligase 2 (New England Biolabs) as a control were used. As substrates, four oligonucleotide fragments in Table 7 were used. An oligonucleotide produced from RNA1-A-13U and RNA1-A-13D was referred to as anti-sense strand, as listed in Table 7. 9.2 µL of solution containing 54 mM Tris-HCl (pH: 7.5), 2.2 mM $MgCl_2$, 1.1 mM dithiothreitol, 0.43 mM ATP, and 0.78 µg/mL of each of the enzymes was placed into a 200-µL microtube, and warmed at 25° C. 23 hours after initiation of warming, 0.2 µL of the substrates in a concentration of 500 µM were added, to initiate a ligation reaction. A composition of the reaction solution was 10 µM oligonucleotide, 50 mM Tris-HCl (pH: 7.5), 2 mM $MgCl_2$, 1 mM dithiothreitol, 0.4 mM ATP, and 0.72 µg/mL of each of the enzymes. 15 minutes after initiation of the reaction, 3 µL of each of the reaction solutions was sampled, and 27 µL of 10 mM EDTA solution was added to terminate the reaction. The amounts of products of the anti-sense strand were determined by HPLC under the condition described in Example 2.

The amounts of products and residual activities in ligation reaction for 15 minutes are listed in Table 8. In a case of using T4 RNA ligase 2 as a control, the amount of the ligation product when the reaction solution was warmed at 25° C. for 23 hours was largely decreased to 19% as compared with a case where the reaction solution was not treated. On the other hand, in a case of using Mut1 having improved ligation activity, the amount of the ligation product when the reaction solution was warmed at 25° C. for 23 hours was 89% of that when the reaction solution was not treated, and the stability was improved.

Similarly, the activity after warming at 37° C. for 4 hours was measured. As listed in Table 9, in a case of using T4 RNA ligase 2 as a control, the amount of the ligation product when the reaction solution was warmed at 37° C. for 4 hours was not confirmed, and the activity was largely decreased. On the other hand, in a case of using Mut1 having improved ligation activity, the amount of the ligation product when the reaction solution was warmed at 37° C. for 4 hours was 83% of that when the reaction solution was not treated, and the stability was improved.

TABLE 7

Sequence used in ligation reaction of four fragments for thermal stability evaluation

| Usage | Name | Sequence | SEQ ID NO |
|---|---|---|---|
| Sense strand, fragment at 5'-end | RNA1-S-12U | AACAGUGUUCUU | 17 |
| Sense strand, fragment at 3'-end | RNA1-S-12D | Pho-GCUCUAUAA | — |
| Antisense strand, fragment at 5'-end | RNA1-A-13U | UUAUAGAGCAAGA | 28 |
| Antisense strand, fragment at 3'-end | RNA1-A-13D | Pho-ACACUGUUUU | 29 |

Pho: Modification of 5'-end with a phosphate group
Upper case letter: DNA

TABLE 8

Production amount and residual activity in ligation reaction for thermal stability evaluation (25° C., 23 h)

| Enzyme | Product concentration (µM) | | Residual activity (%) |
|---|---|---|---|
| | Untreated | 25° C., 23 h | |
| T4 RNA ligase 2 (New England Biolabs) | 3.2 | 0.6 | 19 |
| Mut1 | 4.4 | 3.9 | 89 |

TABLE 9

Production amount and residual activity in ligation reaction for thermal stability evaluation (37° C., 4 h)

| Enzyme | Product concentration (μM) | | Residual activity (%) |
| --- | --- | --- | --- |
| | Untreated | 37° C., 4 h | |
| T4 RNA ligase 2 (New England Biolabs) | 1.9 | 0.0 | 0 |
| Mut1 | 4.8 | 4.0 | 83 |

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A ligase mutant selected from the group consisting of:
(1) a ligase mutant comprising an amino acid sequence showing 95% or more identity to the amino acid sequence of SEQ ID NO: 1, and having a nucleic acid-linking activity;
(2) a ligase mutant comprising an amino acid sequence showing 90% or more identity to the amino acid sequence of SEQ ID NO: 2, and having a nucleic acid-linking activity; and
(3) a ligase mutant comprising an amino acid sequence showing 97% or more identity to the amino acid sequence of SEQ ID NO: 3, and having a nucleic acid-linking activity.

2. The ligase mutant according to claim 1, having a nucleic acid-linking activity for a nucleic acid which is a single-stranded RNA or double-stranded RNA optionally containing DNA and/or a modified nucleic acid.

3. A method for producing a nucleic acid product, said method comprising linking two or more nucleic acid materials in the presence of a ligase mutant according to claim 1 to form said nucleic acid product,
wherein said two or more nucleic acid materials are selected from the group consisting of one or more single-stranded nucleic acid materials, one or more double-stranded nucleic acid materials, and a mixture thereof.

4. The method according to claim 3, wherein said two or more nucleic acid materials are RNA.

5. The method according to claim 3, wherein said two or more nucleic acid materials are four or more single-stranded RNAs.

6. The method according to claim 3, wherein said nucleic acid product contains a complementary portion having a base length of 12 to 27.

7. The method according to claim 3, wherein said two or more nucleic acid materials are DNA and/or a modified nucleic acid.

8. The method according to claim 3, wherein said two or more nucleic acid materials have a concentration of 1 μM or more.

9. The method according to claim 3, wherein said nucleic acid product is siRNA.

10. A polynucleotide encoding a ligase mutant according to claim 1.

11. A polynucleotide encoding a ligase mutant according to claim 2.

12. An expression vector comprising a polynucleotide according to claim 10.

13. An expression vector comprising a polynucleotide according to claim 11.

14. A transformed microorganism comprising an expression unit comprising a polynucleotide encoding a ligase mutant according to claim 1, and a promoter operably linked to the polynucleotide.

15. A transformed microorganism comprising an expression unit comprising a polynucleotide encoding a ligase mutant according to claim 2, and a promoter operably linked to the polynucleotide.

16. A method for producing a ligase mutant, said method comprising producing a ligase mutant according to claim 1 using a transformed microorganism comprising an expression unit comprising a polynucleotide encoding said ligase mutant and a promoter operably linked to said polynucleotide.

* * * * *